US008513192B2

(12) United States Patent
Olsen et al.

(10) Patent No.: US 8,513,192 B2
(45) Date of Patent: Aug. 20, 2013

(54) STABLE GROWTH HORMONE COMPOUNDS RESISTANT TO PROTEOLYTIC DEGRADATION

(75) Inventors: Ole Hvilsted Olsen, Brønshøj (DK); Jens Breinholt, Dyssegård (DK); Christine Bruun Schiødt, Brønshøj (DK); Helle Demuth, Rungsted Kyst (DK); Leif Nørskov-Lauritsen, Tappernøje (DK); Peter Thygesen, Copenhagen Ø (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/144,757

(22) PCT Filed: Jan. 22, 2010

(86) PCT No.: PCT/EP2010/050725
§ 371 (c)(1),
(2), (4) Date: Aug. 30, 2011

(87) PCT Pub. No.: WO2010/084173
PCT Pub. Date: Jul. 29, 2010

(65) Prior Publication Data
US 2011/0306548 A1 Dec. 15, 2011

Related U.S. Application Data

(60) Provisional application No. 61/148,119, filed on Jan. 29, 2009.

(30) Foreign Application Priority Data

Jan. 22, 2009 (EP) ..................... 09151108

(51) Int. Cl.
*A61K 38/27* (2006.01)
*C07K 14/61* (2006.01)

(52) U.S. Cl.
USPC ........................................ 514/11.3; 530/399

(58) Field of Classification Search
None
See application file for complete search history.

(56) References Cited

U.S. PATENT DOCUMENTS

| 4,683,202 A | 7/1987 | Mullis |
| 5,156,956 A | 10/1992 | Motoki et al. |
| 5,252,469 A | 10/1993 | Andou et al. |
| 5,438,040 A | 8/1995 | Ekwuribe |
| 5,545,618 A | 8/1996 | Buckley et al. |
| 5,646,272 A | 7/1997 | Kramer et al. |
| 5,731,183 A | 3/1998 | Kobayashi et al. |
| 5,736,356 A | 4/1998 | Sano et al. |
| 5,834,250 A | 11/1998 | Wells et al. |
| 5,849,535 A | 12/1998 | Cunningham et al. |
| 5,891,840 A | 4/1999 | Cady et al. |
| 5,951,972 A | 9/1999 | Daley et al. |
| 6,004,931 A | 12/1999 | Cunningham et al. |
| 6,057,292 A | 5/2000 | Cunningham et al. |
| 6,136,536 A | 10/2000 | Tomkinson et al. |
| 6,143,523 A | 11/2000 | Cunningham et al. |
| 6,268,343 B1 | 7/2001 | Knudsen et al. |
| 6,358,705 B1 | 3/2002 | Kjeldsen et al. |
| 6,528,486 B1 | 3/2003 | Larsen et al. |
| 6,608,183 B1 | 8/2003 | Cox, III |
| 7,153,930 B1 | 12/2006 | Morrison et al. |
| 2001/0011071 A1 | 8/2001 | Knudsen et al. |
| 2002/0142964 A1 | 10/2002 | Nissen et al. |
| 2003/0162949 A1 | 8/2003 | Cox |
| 2003/0165996 A1 | 9/2003 | Halkier et al. |
| 2004/0001827 A1 | 1/2004 | Dennis |
| 2004/0053370 A1 | 3/2004 | Glaesner et al. |
| 2005/0260237 A1 | 11/2005 | Byun et al. |
| 2006/0094655 A1 | 5/2006 | Guyon et al. |
| 2006/0183197 A1 | 8/2006 | Andersen et al. |
| 2007/0203058 A1 | 8/2007 | Lau et al. |
| 2008/0095837 A1 | 4/2008 | Dinh et al. |
| 2009/0156478 A1 | 6/2009 | Lau et al. |

FOREIGN PATENT DOCUMENTS

| EP | 243929 A2 | 11/1987 |
| EP | 534568 | 3/1993 |
| EP | 555649 A2 | 8/1993 |
| EP | 785276 A1 | 7/1997 |
| EP | 950665 A1 | 10/1999 |
| EP | 1329458 A2 | 7/2003 |
| EP | 05102171.5 | 3/2005 |
| EP | 1704165 A1 | 9/2006 |
| JP | 2000-500505 A | 1/2000 |
| JP | 2002-504527 A | 2/2002 |
| JP | 2002-508162 A | 3/2002 |
| JP | 2003-505347 | 2/2003 |
| JP | 2003-199569 A | 7/2003 |
| JP | 2004-528014 A | 9/2004 |
| JP | 2004-535442 A | 11/2004 |
| JP | 2010-116407 A | 5/2010 |
| RU | 2006107600 A | 10/2007 |
| WO | 90/04788 A1 | 5/1990 |
| WO | 90/11296 | 10/1990 |

(Continued)

OTHER PUBLICATIONS

Alam K S M et al, "Expression and Purification of a Mutant Human Growth Hormone That Is Resistant to Proteolytic Cleavage by Thrombin, Plasmin and Human Plasma In Vitro," Journal of Biotechnology, 1998, vol. 65, Nos. 2-3, pp. 183-190.
Chantalet L et al, "The Crystal Structure of Wild-Type Growth Hormone At 2.5 Å Resolution," Protein and Peptide Letters, 1995, vol. 2, No. 2, pp. 333-340.
De Vos A. M. et al, "Human Growth Hormone and Extracellular Domain of Its Receptor: Crystal Structure of the Complex," Science, 1992, Vol. 255, Issue 5042, pp. 306-312.
Filikov et al, "Computational Stabilization of Human Growth Hormone," Protein Science, 2002, vol. 11, No. 6, pp. 1452-1461.
Garcia-Barros et al., "Proteolytic Processing of Human Growth Hormone (GH) by Rat Tissues In Vitro: Influence of Sex and Age," Journal of Endocrinology, 2000, Vol. 23, pp. 748-754.

(Continued)

*Primary Examiner* — Christine J Saoud
(74) *Attorney, Agent, or Firm* — Jianjie Hu

(57) ABSTRACT

The present invention relates to stable growth hormone (GH) compounds, which through the introduction of cysteine residues have disulphide bridges, which make the compounds resistant to proteolytic degradation.

14 Claims, 4 Drawing Sheets

(56) References Cited

FOREIGN PATENT DOCUMENTS

| | | |
|---|---|---|
| WO | 91/11457 A1 | 8/1991 |
| WO | 92/05271 A1 | 4/1992 |
| WO | 92/09690 A2 | 6/1992 |
| WO | 94/10200 A1 | 5/1994 |
| WO | 96/06931 A1 | 3/1996 |
| WO | 96/12505 A1 | 5/1996 |
| WO | 96/22366 A1 | 7/1996 |
| WO | 96/29342 | 9/1996 |
| WO | 97/11178 A1 | 3/1997 |
| WO | 98/08871 | 3/1998 |
| WO | 98/08872 A1 | 3/1998 |
| WO | 98/38285 A2 | 9/1998 |
| WO | 99/43341 | 9/1999 |
| WO | 99/43361 A1 | 9/1999 |
| WO | 99/43705 A1 | 9/1999 |
| WO | 99/43708 | 9/1999 |
| WO | 9943707 | 9/1999 |
| WO | 00/34331 | 6/2000 |
| WO | 00/69911 | 11/2000 |
| WO | 01/04156 | 1/2001 |
| WO | 01/09163 A2 | 2/2001 |
| WO | 01/12155 A1 | 2/2001 |
| WO | 0151071 | 7/2001 |
| WO | 01/58935 A2 | 8/2001 |
| WO | 0258725 | 1/2002 |
| WO | 02/46227 A2 | 6/2002 |
| WO | 02/055532 A2 | 7/2002 |
| WO | WO 02/055532 | 7/2002 |
| WO | 02/087597 A1 | 11/2002 |
| WO | 02098446 A1 | 12/2002 |
| WO | 03/002136 | 1/2003 |
| WO | 03/013573 A1 | 2/2003 |
| WO | 03/040309 A2 | 5/2003 |
| WO | 03/044056 A2 | 5/2003 |
| WO | 03/087139 A2 | 10/2003 |
| WO | 03/093465 A1 | 11/2003 |
| WO | 2005/014035 A2 | 11/2003 |
| WO | WO 2004/022593 | 3/2004 |
| WO | 2004/065621 A1 | 8/2004 |
| WO | 2004/074315 A2 | 9/2004 |
| WO | 2004/099246 A2 | 11/2004 |
| WO | 2005/014049 A2 | 2/2005 |
| WO | 2005/027978 | 3/2005 |
| WO | 2005/027978 A2 | 3/2005 |
| WO | 2005/028516 A2 | 3/2005 |
| WO | 2005/035553 A2 | 4/2005 |
| WO | 2005/058958 A2 | 6/2005 |
| WO | 2005/070468 A2 | 8/2005 |
| WO | 2006/005667 A2 | 1/2006 |
| WO | 2006/013202 A2 | 2/2006 |
| WO | 2006/037810 A2 | 4/2006 |
| WO | WO 2006/048777 | 5/2006 |
| WO | 2006/097536 A2 | 9/2006 |
| WO | 2006/097537 | 9/2006 |
| WO | 2006/097537 A2 | 9/2006 |
| WO | 2006/097538 A1 | 9/2006 |
| WO | 2006/134173 A2 | 12/2006 |
| WO | 2007/020290 A1 | 2/2007 |
| WO | 2007/093594 A1 | 8/2007 |
| WO | 2008/003750 A2 | 1/2008 |
| WO | 2008/014430 A1 | 1/2008 |
| WO | 2008/020075 A1 | 2/2008 |
| WO | 2008/027854 A2 | 3/2008 |
| WO | 2008/101240 A1 | 8/2008 |
| WO | 2009/030771 A1 | 3/2009 |
| WO | 2010/015668 A1 | 2/2010 |
| WO | 2010/029159 A1 | 3/2010 |
| WO | 2010/084173 A1 | 7/2010 |

OTHER PUBLICATIONS

Kasimova, MR et al., "NMR Studies of the Bacbone Flixibility and Structure of Human Growth Hormone: A Comparison of High and Low Ph Conformations," Journal of Molecular Biology, 2002, vol. 318, pp. 679-695.

Lewis, UJ et al., "Variants of Growth Hormone and Prolactin and Their Posttranslational Modifications," Annual Review of Physiology, 1984, Vol. 46, pp. 33-42.

Frostell-Karlsson et al., Journal of Medicinal Chemistry, "Albumin Binding Property", 2000, vol. 43, No. 10, pp. 1986-1992.

Berge et al., Journal of Pharmaceutical Sciences, "Pharmaceutical Salts", 1977, vol. 66, No. 1, pp. 1-19.

Masters, "Applications of Spray Drying," in Spray-Drying Handbook (5.sup.th ed; Longman Scientific and Technical), pp. 491-676 (1991).

Altschul et al, -, "Blast Manual" downloaded Jan. 10, 2013.

Altschul et al., Journal of Molecular Biology "BLASTP, BLASTN, and FASTA", 1990, vol. 215, No. -, pp. 403-410.

B. Lee and F.M. Richards, Journal of Molecular Biology, "The Interpretation of Protein Structures: Estimation of Static Accessibility", 1971, vol. 55, No. -, pp. 379-400.

B. Peschke et al., Bioorganic & Medicinal Chemistry, "C-Terminally Pegylated HGH Derivatives", 2007, vol. 15, No. -, pp. 4382-4395.

Broadhead et al., Drug Delivery, "The Spray Drying of Pharmaceuticals", 1992, vol. 18, No. 11 & 12, pp. 1169-1206.

C. A. Lipinski et al., Advanced Drug Delivery Reviews, "Experimental and Computational Approaches to Estimate Solubility and Permeability in Drug Discovery and Development Settings", 1997, vol. 23, pp. 3-25.

Carpenter and Crowe, Cryobiology, "Modes of Stabilization of a Protein by Organic Solutes During Dessication", 1988, vol. 25, No. -, pp. 459-470.

Dayhoff et al., -, "Atlas of Protein Sequence and Structure", 1978, vol. 5, No. 3, Pages-.

G. T. Hermanson, -, "Bioconjugate Techniques, Elsevier", 2008, vol. 2, Number-, Pages-.

I. Moriguchi, S. Hirono, I. Nakagome, H. Hirano, Chemical & Pharmaceutical Bulletin, "Comparison of Reliability of LOGP Values for Drugs Calculated by Several Methods", 1994, vol. 42, Number-, pp. 976-978.

Kurtzhals, P et al., Biochemical Journal, "Albumin Binding of Insulins Acylated With Fatty Acides . . . ", 1995, vol. 312, Number-, pp. 725-731.

Kaempfer, Journal of General Microbiology, "Genus *Streptomyces*", 1991, vol. 137, Number-, pp. 1831-1892.

M. M. Kurfurst, Analytical Biochemistry, "-", 1992, vol. 200(2), Number-, pp. 244-248.

Mumenthaler et al.,, Pharmaceutical Research, "Feasibility Study on Spray-Drying Protein Pharmaceuticals: Recombinant Human Growth Hormone and Tissue-Type Plasminogen Activator", 1994, vol. 11, No. 1, pp. 41263.

Chene, N., "Growth hormones. II. Structure-function relationships," Reprod. Nutr. Dev., 1989. , 29 1-25.

Roser, Biopharmaceutical, "Trehalsoe Drying: A Novel Replacement for Freeze Drying", 1991, vol. 4, Number-, pp. 47-53.

Sato, H, Advanced Drug Delivery Reviews, "Enzymatic Procedure for Site-Specific Pegylation of Proteins", 2002, vol. 54, Number-, pp. 487-504.

T. Fujita; J. Iwasa and C. Hansch, Journal of the American Chemical Society, "A New Substituent Constant, PI, Derived From Partition Coefficients", 1964, vol. 86, Number-, pp. 5175-5180.

Wada, E et al., Biotechnology Letters, "Enzymatic Modification of . . . ", 2001, vol. 23, Number-, pp. 1367-1372.

Williams and Polli, Journal of Parenteral Science & Technology, "The Lyophilization of Pharmaceuticals: A Literature Review", 1984, vol. 38, No. 2, pp. 48-59.

Gregory J. Russel-Jones and David H. Alpers, Membrane Transporters As Drug Targets, 1999, Chapter 17, New York.

Alexander Deitrs,et al, Journal of the American Chemical Society, "Adding Amino Acids With Novel Reactivity to the Genetic Code of *Saccharomyces cerevisiae*", 2003, vol. 125, 39, pp. 11782-11783.

Altschul SF, Madden TL, Schäffer AA, Zhang J, Zhang Z, Miller W, Lipman DJ. Gapped BLAST and PSI-BLAST: a new generation of protein database search programs. Nucleic Acids Res. Sep. 1, 1997;25(17):3389-402.

Beaucage&CaruthersTetrahedron Lettersdeoxynucleoside Phosphoramidites-A New Class of Key Intermediates for Deoxypolynucleotide Synthesis198122201859-1862.

Cabrita,et al, Biotechnology Annual Reviewprotein Expression and Refolding—A Practical Guide to Getting the Most Out of Inclusion Bodies, 2004, vol. 10, pp. 31-50.
Carillo,et al, Journal of Applied Mathametics "The Multiple Sequence Alignment Problem in Biology" 1988 vol. 48 Part 5 pp. 1073-1082.
Chalasani et al, Journal of the Controlled Releasea Novel Vitamin B12-Nanosphere Conjugate Carrier System for Peroral Delivery of Insulin, 2007, vol. 117, pp. 421-429.
Chin et al, Science, An Expanded Eukaryotic Genetic Code, 2003, vol. 301,pp. 964-967.
Devereux et alNucleic Acids Researcha Comprehensive Set of Sequence Analysis Programs for the VAX, 1984, vol. 12, No. 1, pp. 387-395.
Dombkowski A, Bioinformatics, Disulfide by Design:A Computational Method for the Rational Design of Disulfide Bonds in Proteins, 2003, vol. 19, No. 14, pp. 1852-1853.
Greene, et al Protective Groups in Organic Chemistry Synthesis Protective Groups in Organic Synthesis 2006 9-0-471.
M. Gribskov, J. Devereux, Sequence Analysis Primer, Stockton Press, NewYork and Macmillan, Basingstroke (1991), pp. 90-157.
Griffin,et al Humana Press, Totowa New Jersey "Methods in Molecular Biology vol. 24: Computer Analysis of Sequence Data Part I" 1994.
Gumbleton.M, Advanced Drug Delivery Reviews, Caveolae As Potential Macromolecule Trafficking Compartments Within Alveolar Epithelium, 2001, vol. 49, No. 3, pp. 281-300.
H. Li & Z. M.Qian, Medicinal Research Reviews. Transferrin/Transferrin Receptor-Mediated Drug Delivery, 2002, vol. 22, No. 3, pp. 225-250.
Henikoff,et al Proceedings of the National Academy of Sciences of the USA Amino Acid Substitution Matrices Form Protein Blocks 1992 89—10915-10919.
Kondoh.et al, Molecular Pharmacology, A Novel Strategy for the Enhancement of Drug Absorption Using a Claudin Modulator, 2005 vol. 67, No. 3, pp. 749-756.
Lee et al, Biotechnology and Applied Biochemistry, Expression and Characterization of Human Growth Hormone-FC Fusion Proteins for Transcytosis Induction, 2007, vol. 46, pp. 211-217.
Lei Wang,et al, Science, Expanding the Genetic Code of *Escherichia coli*, 2001, vol. 292, pp. 498-500.
Leitner.V.M.et al European Journal of Pharmaceutics and Biopharmaceutics : Official Thiolated Ploymers: Evidence for the Formation of Disulphide Bonds With Mucus Glycoproteins 2003 56—207-214.
Lesk.A.M Oxford University Press Computational Molecular Biology: Sources and Methods for Sequence Analysis 19881—254.
Leuben.H.L.et al International Journal of Pharmaceutics Mucoadhesive Polymers in Personal Peptide Drug Delivery.V.Effect of Poly(Acrylates)on the Enzymatic of Peptide Drugs by Intestinal Brush Border Membrane Vesicles 1996, vol. 141, Nos. 1-2, pp. 39-52.
Liang & Young, Biochemical and Biophysical Research Communications, Insulin-Cell Penetrating Peptide Hybrids With Improved Intestinal Absorption Efficiency, 2005, vol. 335, pp. 734-738.
Lueben.H.L.et al Pharmaceutical Research Mucoadhesive Polymers in Peroral Peptide Drug Delivery .VI.Carbomer and Chitosan Improve the Intestinal Absorption of the Peptide Drug Buserelin In Vivo, 1996, vol. 13, No. 11, pp. 1668-1672.
Masuda.N,et al Biochimica Et Biophysica Acta Molecular Cloning of CDNA Encoding 2O KDO Variant Human Growth Hormone and the Alternative Splicing Mechanism 1988 949 1 125-131.
Matthes,et al EMBO Journal Simultaneous Rapid Chemical Synthesis of Over 100 Oligonucleotides on a Microscale 1984 3 4 801-805.
Needeleman,et al Journal of Molecular Biology a General Method Applicable to the Search for Similarities in the Amino Acid Sequence of Two Proteins 1970 48—443-453.
Makino et al., 2005, "Semisynthesis of Human Ghrelin: Condensation of a Boc-Protected Recombinant Peptide With a Synthetic O-Acylated Fragment," Biopolymers 79(5):238-247.
Okada, 2001, "Synthesis of Peptides by Solution Methods," Current Organic Chemistry 5(1):1-43.

Ostrovsky, 1975, "Comparative Characteristics of the Hydrophobic Nature of Certain Proteins by Their Interaction With 2-P Toluidino," Ukrayins'kyi Biokhimichnyi Zhurnal 47(6):701-707.
Picó, 1990, "Use of 1-Anilino-8-Naphthalene Sulfonate As a Reporter Molecule to Study the Bile Salts-Bovine Serum Albumin Binding," Studia Biophysica 136(1):21-26, Abstract XP-008039734.
Rudinger, 1976, "Characteristics of the Amino Acids As Components of a Peptide Hormone Sequence," Peptides Hormones, JA Parsons Edition, University Park Press, Jun. 1976, pp. 1-7.
Schinzel et al., 1991, "The Phosphate Recognition Site of *Escherichia coli* Maltodextrin Phosphorylase," Federation of European Biochemical Society Jul. 1991, 286(1, 2):125-128.
Sheffield, 2001, "Modification of Clearance of Therapeutic and Potentially Therapeutic Proteins," Current Drug Targets Cardiovascular & Haematological Disorders 1(1):1-22.
SIGMA GENOSYS (Web Site), Designing Custom Peptides, pp. 1-2, Accessed Dec. 16, 2004.
Voet et al., 1995, Biochemistry 2nd ed., John Wiley & Sons, Inc., pp. 235-241.
Wallace, 1995, "Peptide Ligation and Semisynthesis," Current Opinion in Biotechnology 6(4):403-410.
Zobel et al., 2003, "Phosphate Ester Serum Albumin Affinity Tags Greatly Improve Peptide Half-Life In Vivo," Bioorganic & Medicinal Chemistry Letters 13:1513-1515.
Knudsen, L.B. et al., "Potent Derivatives of Glucagon-Like Peptide-1 With Pharmacokinetic Properperties Suitable for Once Daily Administration", Journal of Medicinal Chemistry, 2000 vol. 43, pp. 1664-1669.
Deacon, C.F. et al., "Dipeptidyl peptidase IV resistant analogues of glucagon-like peptide-1 which have extended metabolic stability and improved biological activity." 1998, Diabetologia, vol. 41, pp. 271-278.
Kurtzhals, P, et al., "Albumin Binding of Insulins Acylated With Fatty Acids: Characterization of the Ligand-Protein Interaction and Correlation Between Binding Affinity and Timing of the Insulin Effect In Vivo," Biochem J, 1995, vol. 312, pp. 725-731.
Watanabe et al., "Structure-Activity Relationships of Glucagon-Like Peptide-1 (7-36) Amide: Insulinotropic Activities in Perfused Rat Pancreases, and Receptor Binding and Cyclic AMP Production in RINm5F Cells," Journal of Endocrinology, 1994, vol. 140, pp. 45-52.
Jung-Guk Kim et al. Diabetes Development and Characterization of a Glucagon-Like Peptide 1-Albumin Conjugate/ The Ability to Activate the Glucagon-Lile Peptide 1 Receptor In Vivo 2003 52—751-759.
Definition of Moiety, From http://dictionary.reference.com/browse/moiety, pp. 1-2. Accessed Aug. 26, 2010.
Small Bowel Syndrome from e-Medicine, pp. 1-12, Accessed Sep. 24, 2008.
Alam K S M et al, Journal of Biotechnology, "Expression and Purification of a Mutant Human Growth Hormone That is Resistant to Proteolytic Cleavage by Thrombin, Plasmin and Human Plasma In Vitro", 1998, vol. 65, No. 2-3, pp. 183-190.
Carey et al, The Liver: Biology and Pathobiology 2nd Edition, Raven Press Ltd, "Enterohepatic Circulation", 1988, vol. 33, pp. 573-616.
Devos A. M. et al, Science, "Human Growth Hormone and Extracelleular Domain of Its Receptor: Crystal Structure of the Complex", 1992, vol. 255, pp. 306-312.
Palmberger.et al European Journal of Pharmaceutics and Biopharmaceutics : Official Thiolated Polymers: Evaluation of the Influenece of the Amount of Covalently Attached L-Cysteine to Poly(Acrylic Acid) 2007 66—405-412.
Partlow.K.C.et al Biomaterials Exploiting Lipid Raft Transport With Membrane Targeted Nanoparticles:A Strategy for Cytosolic Drug Delivery 2008 29—3367-3375.
Petersen,et al Protein Engineering Amino Acid Neighbours and Detailed Conformational Analysis of Cysteines in Proteins 1999 12 7 535-548.
S.Y.Chae,et al Bioconjugate Chemistry Preparation, Characterization and Application of Biotinylated and Biotin-Pegylated Glucagon-Like Peptide-1 Analogues for Enhanced Oral Delivery 2008 19—334-341.

Said, Hamid M; Mohammed, Zainab M. Current Opinion in Gastroenterology Intestinal Absorption of Watersoluble Vitamins: an Update 2006 22 2 140-146.
Saiki, et al Science Primer-Directed Enzymatic Amplification of DNA With a Thermostable DND Polymerase 1988 239 4839 487-491.
Takatsuka.et al European Journal of Pharmaceutics and Biopharmaceutics : Official Enhancement of Intestinal Absorption of Poorly Absorbed Hydrophilic Compounds by Simultaneous Use of Mucolytic Agent and Non-Ionic Surfacant 2006 62—52-58.
Von Heijne.G Academic Press Sequence Analysis of Molecular Biology. Treasure Torve or Trivial Pursuit 1987—188.
Zhiwen Zhang et al, Science, A New Strategy for the Synthesis of Glycoproteins, 2004 vol. 303, pp. 371-373.
Szente et al., "Solubilization of Fatty Acids and Similar Lipids by Methylated Cyclodextrins," Proceedings of the International Symposium on Cyclodextrins, Jan. 1, 1992, pp. 340-344.
Szejtli, Jozsef, Cyclodextrin Technology (A book), Published by Springer, 1988, p. 271.
Dennis, MS et al., Journal of Biological Chemistry, "Albumin Binding As a General Strategy for Improving the Pharmacokinetics of Proteins", 2002, vol. 277, No. 28 pp. 35035-35043.
Pasut, G et al., Expert Opinion on Therapeutic Patents, "Protein, Peptide and Non-Peptide Drug Pegylation . . . " 2004, vol. 14, No. 6, pp. 859-894.
Bebernitz et al., Journal of Medicinal Chemistry, "Reduction in Glucose Levels in STZ Diabetic Rats by 4-(2,2-Dimethyl-1-Oxopropyl) Benzoic Acid: A Prodrug Approach for Targeting the Liver" 2001 vol. 44 pp. 512-523.
Beljaars et al., Journal of Drug Targeting, "Neoglyco-And Neopeptide Albumins for Cell-Specific Delivery of Drugs to Chronically Diseased Livers" 2001 vol. 115 pp. 189-240.
Biessen et al., Journal of Medicinal Chemistry, "Synthesis of Cluster Galactosides With High Affinity for the Hepatic Asialoglycoprotein Receptor" 1995 vol. 38 Part 9 pp. 1538-1546.
Hatori et al., Journal of the Controlled Release, "Controlled Biodistribution of Galactosylated Liposomes and Incorporated Probucol in Hepatocyte-Selective Drug Targeting" 2000 vol. 69 pp. 369-377.
Kim et al., Journal of Drug Targeting, "Evaluation of the Bile Acid Transporter in Enhancing Intestinal Permeability to Renininhibitory Peptides" 1993 vol. 1 pp. 347-359.
Kramer et al., Journal of Biological Chemistry, "Liver-Specific Drug Targeting by Coupling to Bile Acids", 1992 vol. 267 Part 26 pp. 18598-18604.
Kramer et al., Journal of the Controlled Release, "Modified Bile Acids As Carriers for Peptides and Drugs", 1997 vol. 46 Part 1-2 pp. 17-30.
Kramer et al., Journal of Biological Chemistry, "Intestinal Absorption of Peptides by Coupling to Bile Acids" 1994 vol. 269 Part 14 pp. 10621-10627.
Kullack-Ublick et al., Gastroenterology, "Chlorambucil-Taurocholate Is Transported by Bile Acid Carriers Expressed in Human Hepatocellular Carcinomas" 1997, vol. 113 pp. 1295-1305.
Leeson et al., Journal of Medicinal Chemistry, "Selective Thyromimetics. Cardiac-Sparing Thyroid Hormone Analogues Containing 3'-Arylmet HYL Substituents" 1989 vol. 32 Part 2 pp. 320-326.
Nezasa et al., Drug Metabolism and Disposition, "Liver-Specific Distribution of Rosuvastatin in Rats: Comparison With Pravastatin and Simvastatin" 2002 vol. 30 Part 11 pp. 1158-1163.

Pecher et al., Biophysical Chemistry, "The Effect of Additional Disulfide Bonds on the Stability and Folding of Ribonuclease" 2009 vol. 141 Part 1 pp. 21-28.
Starke et al., Bioorganic & Medicinal Chemistry Letters, "Bile Acid-Oldigodeoxynucleotide Conjugates: Synthesis and Liver Excretion in Rats", 2001 vol. 11 pp. 945-949.
Swaan, PW et al., Bioconjugate Chemistry, "Enhanced Transepithelial Transport of Peptides by" 1997 vol. 8 Part 4 pp. 520-525.
Wess et al., Tetrahedron Letters, "Modified Bile Acids: Preparation of 7A, 12A-Dihydroxy-3a- and 7A, L2A-Dihydroxy-3A-(2-Hydroxyethoxy)-SIJ-Cholanic Acid and Their Biological Activity" 1992, vol. 33 Part 2 pp. 195-198.
Inflammatory Bowel Disease from e-Medicine, pp. 1.24, Accessed Sep. 24, 2008.
Ngo JT et al., "Computational Complexity, Protein Structure Prediction, and the Levinthal Paradox," The Protein Folding Problem and Tertiary Structure Prediction, K. Mere Jr. and S. LeGrand Edition, 1994, pp. 433-495.
Residue definition from www.dictionary.com, pp. 1-6, Accessed May 5, 2009.
Green, Brian D. et al Biological Chemistry. Degradation, Receptor Binding, Insulin . . . 2004 385 2 169-177.
Greenwald Journal of the Controlled Release PEG Drugs: An Overview 2001 74—159-171.
Ji, J. et al. Biomaterials Stearyl Poly (Ethylene Oxide) Grafted Surfaces for Preferential Adsorption of Albumin. 2001 22—3015-3023.
Knudsen, L.B. Journal of Medicinal Chemistry Glucagon-Like Peptide-1 . . . 2004 47—4128-4134.
Simonovsky et al. Journal of Biomaterials Science, Polymer Edition Poly(Ether Urethane)s Incorporating Long Alkyl Side-Chains With Terminal Carboxyl Groups as Fatty Acid Mimics: Synthesis, Structural Characterization and Protein Adsorption 2005 16 12 1463-1483.
Soltero and Ekwurlbe Innovations in Pharmaceutical Technology the Oral Delivery of Protein and Peptide Drugs. 2001 1—106-110.
Still, J. Gordon, Diabetes/Metabolism Research Reviews, Development of Oral Insulin: Progress and Current Status, 2002, vol. 18, Suppl 1, pp. S29-S37.
Veronese F. M Biomaterials Peptide and Protein Pegylation: A Review of Porblems and Solutions 2001 22 5 405-417.
English abstract of JP 2004535442.
English abstract of RU 2006107600.
English abstract of JP 2010116407.
English abstract of JP 2004528014.
Berendsen, 1998, "A Glimpse of the Holy Grail?" Science 282:642-643.
Bradley et al., 2002, "Limits of Cooperativity in a Structually Modular Protein: Response of the Notch Ankyrin Domain to Analogous Alanine Substitutions in Each Repeat," Journal of Molecular Biology 324:373-386.
Chuang et al., 2002, "Pharmaceutical Strategies Utilizing Recombinant Human Serum Albumin," Pharmaceutical Research 19(5):569-577.
Han, 2002, "Targeted Prodrug Design to Optimize Drug Delivery," AAPS Pharmsci 2(1):1-11.
Hodgson et al., 2004, "The Synthesis of Peptides and Proteins Containing Non-Natural Amino Acids," Chemical Reviews 33(7):422-430.
Holz et al., 2003, "Glucagon-Like Peptide-1 Synthetic Analogs: New Therapeutic Agents for Use in the Treatment of Diabetes Mellitus," Current Medicinal Chemistry 10(22):2471-2483.
Kim et al., 2003, "Development and Characterization of a Glucagon-Like Peptide 1-Albumin Conjugate," Diabetes 52:751-759.

Figure 2

```
1    FPTIPLSRLF DNAMLRAHRL HQLAFDTYQE FEEAYIPKEQ KYSFLQNPQT SLCFSESIPT
                H1                                            L1
61   PSNREETQQK SNLELLRISL LLIQSWLEPV QFLRSVFANS LVYGASDSNV YDLLKDLEEG
                    H2                              L2           H3
121  IQTLMGRLED GSPRTGQIFK QTYSKFDTNS HNDDALLKNY GLLYCFRKDM DKVETFLRIV
                   L3                                        H4
181  QCRSVEGSCG F
```

STABLE GROWTH HORMONE COMPOUNDS RESISTANT TO PROTEOLYTIC DEGRADATION

CROSS-REFERENCE TO RELATED APPLICATIONS

This application is a 35 U.S.C. §371 national stage application of International Patent Application PCT/EP2010/050725 (published as WO 2010/084173), filed Jan. 22, 2010, which claimed priority of European Patent Application 09151108.9, filed Jan. 22, 2009; this application further claims priority under 35 U.S.C. §119 of U.S. Provisional Application 61/148,119, filed Jan. 29, 2009.

FIELD OF INVENTION

The present invention relates to stable growth hormone (GH) compounds resistant to proteolytic degradation.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Jul. 13, 2011. The Sequence Listing is made up of 3 kilobytes, and the information contained in the attached "SEQUENCE LISTING" is identical to the information in the specification as originally filed. No new matter is added.

BACKGROUND OF INVENTION

Growth hormone (GH) is a polypeptide hormone secreted by the anterior pituitary in mammals. Dependent on species GH is a protein composed of approximately 190 amino acid residues corresponding to a molecular weight of approximately 22 kDa. GH binds to and signals through cell surface receptors, the GH receptors (GHR). GH plays a key role in promoting growth, maintaining normal body composition, anabolism and lipid metabolism. It also has direct effects on intermediate metabolism, such as decreased glucose uptake, increased lipolysis, increased amino acid uptake and protein synthesis. The hormone also exerts effects on other tissues including adipose tissue, liver, intestine, kidney, skeleton, connective tissue and muscle. Recombinant hGH has been produced and commercially available as, for ex: Genotropin™ (Pharmacia Upjohn), Nutropin™ and Protropin™ (Genentech), Humatrope™ (Eli Lilly), Serostim™ (Serono), Norditropin (Novo Nordisk), Omnitrope (Sandoz), Nutropin Depot (Genentech and Alkermes). Additionally, an analogue with an additional methionine residue at the N-terminal end is also marketed as, for ex: Somatonorm™ (Pharmacia Upjohn/Pfizer).

GH shares a common topology with the other members of the GH-family of proteins, Prolactin (PRL) and Placental Lactogen (PL). GH is classified as a four-helix bundle protein (FIG. 1) exhibiting an "up-up-down-down" topology with two conserved disulphide linkages. Specifically, wild-type human GH (hGH) is composed of 191 amino acid residues and has four cysteine residues at positions 53, 165, 182 and 189, which stabilizes the three dimensional structure of the protein by forming two intramolecular disulphide bonds connecting C53 with C165 and C182 with C189, respectively (FIG. 1). The structure of hGH has been experimentally determined by X-ray crystallography in the free form (Chantalet L. et al (1995) Protein and Peptide Letters 3, 333-340) and in complex with its binding protein (the extra cellular domain of the human GHR (hGHR)) (Devos, A. M. et al (1992) Science 255, 306-312). These structures have been deposited in the Protein Data Bank (PDB) and are publicly available (PDB accession codes 1HGU and 1HWG, respectively). Thus, from the published hGH structures residues important for hGH binding to hGHR can be identified. Furthermore, the dynamic properties of hGH has been studied by Nuclear Magnetic Resonance (NMR) spectroscopy (Kasimova M. R. et al. J. Mol. Biol. (2002) 318, 679-695). In combination, the X-ray and NMR data can distinguish regions of hGH which are well structured and well defined from regions which are less structured and dynamic. Less structured and dynamic regions of hGH are expected to be particularly susceptible to proteolytic cleavage and proper stabilization of such regions would lead to improved proteolytic stability.

hGH has been subject to extensive mutagenesis in attempts to produce hGH analogues with desired chemical or biological properties. Specifically, cysteine mutants for several purposes have been described.

US 2003/0162949 disclose cysteine variants of members of the GH supergene family. A general method is provided for creating site-specific, biologically active conjugates of these proteins. The method involves adding cysteine residues to non-essential regions of the proteins or substituting cysteine residues for non-essential amino acids in the proteins using site-directed mutagenesis and then covalently coupling a cysteine-reactive polymer or other type of cysteine-reactive moiety to the proteins via the added cysteine residue WO 02/055532 describes genetically engineered hGH mutants having at least one non-polypeptide moiety covalently attached, particularly hGH mutants where a introduced cysteine residue was used for pegylation.

U.S. Pat. No. 5,951,972 describes physiologically active derivatized natural and recombinant mammalian and human proteins and polypeptides wherein at least one-naturally-occurring or incorporated cysteine residue within the protein is derivatized with various substituents.

The proteolytic cleavage of hGH has been studied in detail. The long loop composed of residues 128 to 154 has putative cleavage sites for several proteases, such as thrombin, plasmin, collagenase, subtilisin and chymotrypsin-like serine proteases. Accordingly, this part of hGH has been shown to be particularly susceptible to proteolytic cleavage (Lewis, U. J. Ann. Rev. Physiol. (1984.) 46, 33-42). Enzymes reported to degrade hGH include thrombin, plasmin, subtilisin, chymotrypsin-like serine proteinases and kallikreins.

The degradation of hGH in rat tissue has been investigated (Garcia-Barros et al. J. Endocrinol. Invest. (2000) 23, 748-754).

In rat thyroid gland chymotrypsin-like proteases, favouring cleavage at bulky and lipophilic amino acid residues, were found initially to cleave the peptide bond between Y143 and S144 resulting in a two chain molecule, followed by cleavage between Y42 and S43, liberating the N-terminal peptide F1-Y42. The split loop in the two chain molecule is processed further by cleavage between F146 and D147 by chymotrypsin-like proteases and further by the action of carboxypeptidases.

Several methods to produce hGH analogues stabilized towards proteolytic degradation have been reported.

Alam et al., J. Biotech. 65, 183-190 (1998)) designed hGH mutants resistant to thrombin and plasmin by specific point mutations. Thrombin cleaves hGH specifically between R134 and T135, and the double mutant R134D, T135P yielded a hGH variant resistant to cleavage by thrombin, and the triple mutant R134D, T135P, K140A resulted in resistance to plasmin. Furthermore, the latter hGH mutant was resistant to proteolysis by human plasma over a period of 7 days.

EP534568 describes hGH mutants stabilized towards proteolytic degradation by mutating R134 to alanine, leucine, threonine, phenylalanine, proline or histidine.

WO2004022593/Nautilus describes general high throughput directed evolution methods to produce modified cytokines, including GH variants, with increased proteolytic stability.

WO2006048777/Nautilus specifically describes modified hGH analogues with improved proteolytic stability. The analogues contain one to five mutations at positions 1-55, 57, 58, 60-63, 67-87, 89-91, 93, 95-100, 102-128, 131-132, 135-139, 141, 142, 144, 148-182, 184, 185 and 187-191. Introduction of cysteine residues can potentially lead to the formation of undesired disulfide linked dimers and in WO2006048777 the substitution of amino acid residues by cysteine is specifically excluded from the scope; in WO2006048777 (p. 65) it is stated: "The replacement of amino acids by cysteine residues is explicitly avoided since this change would potentially lead to the formation of intermolecular disulfide bonds".

There is an obvious need to develop hGH compounds which are resistant to proteolytic degradation. Such stabilized compounds should exhibit increased stability towards proteolytic cleavage while retaining the desired biological properties of hGH. Such GH molecules would have increased stability, slower clearance and/or prolong in vivo half-life.

Furthermore protein therapeutics generally needs to be administered intravenously or subcutaneously because they are generally not sufficiently orally available. The low oral bioavailability of proteins is partly due to proteolytic degradation in the gastrointestinal tract. Hence, there is also a need to develop hGH compounds that can be administered orally to treat hGH related disorders.

SUMMARY OF INVENTION

The present invention relates to hGH compounds comprising additional disulfide bonds. In the hGH compounds of the present invention at least one additional cysteine residue has been introduced by mutating at least one amino acids in the wild-type hGH sequence to cysteine. In the hGH compounds of the present invention the sites of mutation are chosen in such a way that (1) the introduced cysteine residue(s) is (are) appropriately placed in the three dimensional structure of the folded protein to allow for the formation of additional disulphide bonds not present in the wild type protein (2) the native structure of hGH is not disrupted (3) the hGH compound exhibits increased stability towards proteolytic cleavage compared to wild type hGH or other enhanced functionalities and (4) the hGH compound retains the desired biological activities associated with wild type hGH. Such disulphide variants of hGH compounds resistant to proteolytic degradation in the gastro intestinal tract can be developed as orally administered drugs for treating hGH related disorders.

Figure 1:
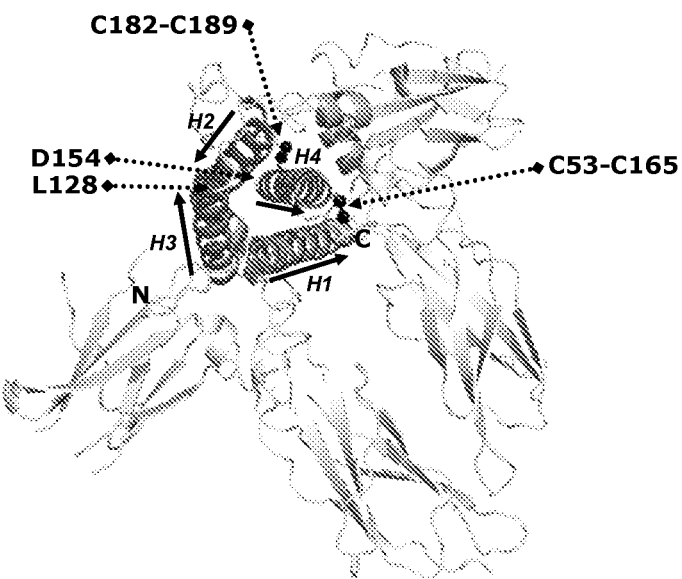
FIG. 1
Figure 3A:
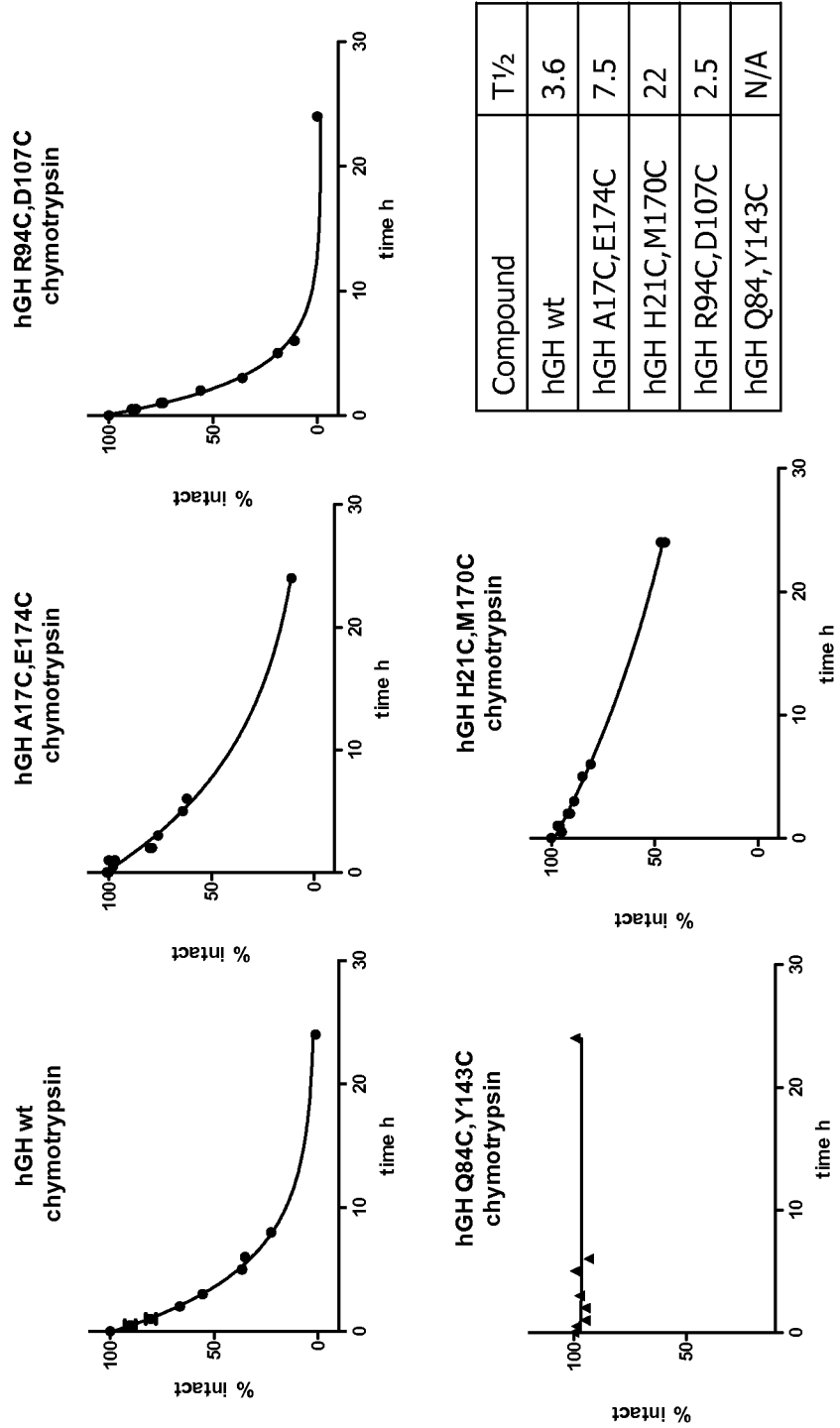
Figure 3B:
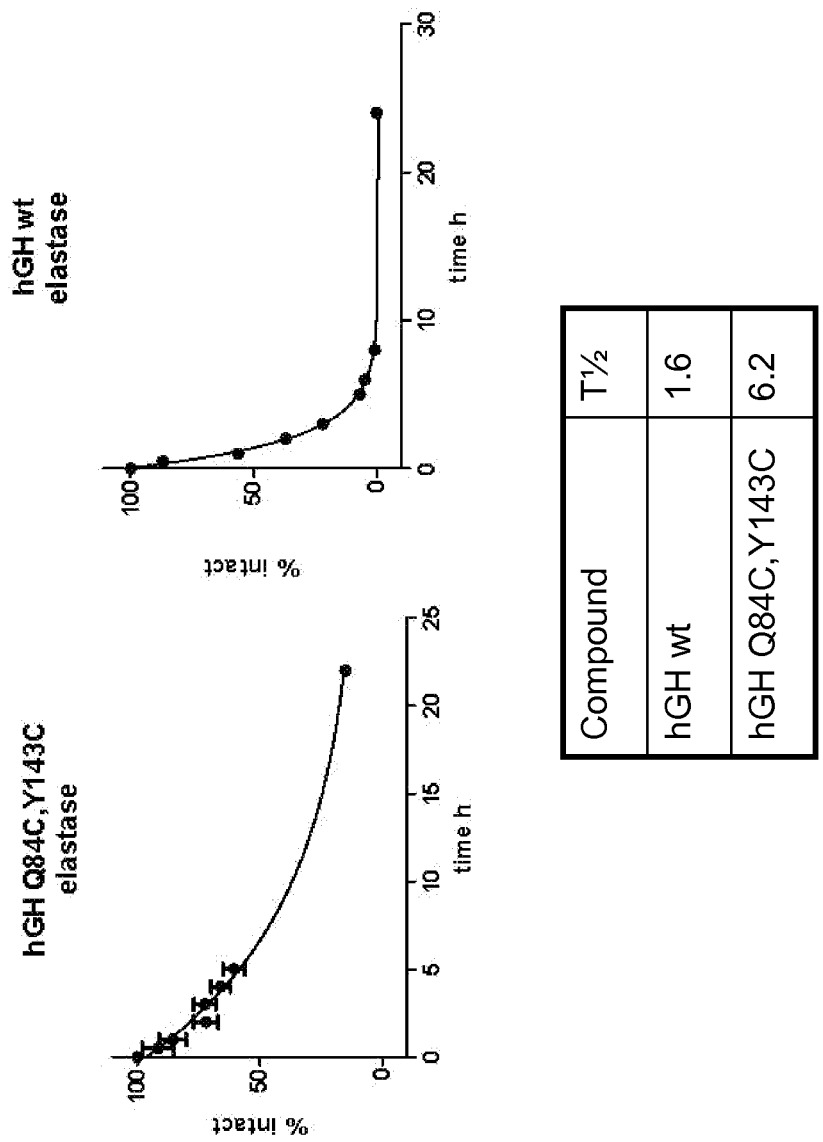

Structure of hGH bound to two copies of the hGH binding protein (PDB 1HWG). The four major helices in hGH are shown in dark gray and are labeled H1-H4. The directions (N→C terminal) are indicated by arrows. The N- and C-termini of hGH are labeled N and C, respectively. The two disulphide bonds connecting C53 with C165 and C182 with C189, respectively, are represented by black sticks and balls. Also labeled are L128 and D154 representing the first and last residues, respectively, in the long flexible loop connecting H3 and H4.

FIG. 2

Wild type amino acid sequence of hGH with the four main helices (H1-H4) highlighted and labeled. Also labeled are the three loops (L1-L3) connecting the main helices. The helix definitions refer to hGH in complex with its binding protein (PDB 1HWG).

FIG. 3

Time course for the proteolytic digestion of wild type hGH and hGH compounds with additional disulfide bonds. The proteases used are chymotrypsin (panel A) and elastase (panel B). Assay is conducted as described in Example 5. The amount of intact protein (in % relative to t=0) is plotted against incubation time. T½ (hours) derived by fitting the data to single exponentials are listed in the tables.

DETAILED DESCRIPTION OF THE INVENTION

The present invention relates to stable hGH compounds having additional disulphide bonds. The disulphide bonds are formed between pairs of cysteines of which one or both are introduced by point mutations in the wild type hGH sequence. The sites of mutation are chosen such that the introduced cysteine residues are appropriately placed in the three dimensional structure of the folded protein to allow for the formation of a disulphide bond. If only one cysteine is introduced, its partner in forming a disulphide bond will include one of the four cysteine residue present in wild type hGH. The folded protein with the additional disulphide bond may be obtained by expressing the appropriate cysteine mutant of hGH in soluble form by a suitable host organism, or recovered from inclusion bodies using standard refolding conditions for growth hormone compounds, which are well known to those skilled in the art (Cabrita and Bottomley, Biotechnology Annual Review 10, 31-50 (2004)). The identification of candidate positions for introduction of additional disulphide bonds can be aided by computational methods, e.g. using the experimentally determined three dimensional structure of hGH (PDB accession code 1HWG) in complex with two copies of its binding protein. Selection of appropriate positions for introduction of disulphide bond can be based distance and geometry criteria for disulphide bonds described in Dombkowski A., A., Bioinformatics 19, 1852-1853 (2003) and Petersen et al., Protein Eng. 12, 535-548 (1999).

The cysteine mutants are chosen such that the introduced disulphide bonds do not disrupt the native structure of the protein and have minimal negative impact on the desired biological activity associated with hGH. Thus, the compounds are constructed such that the introduced disulphide bonds do not impair interaction with hGHR. The regions in hGH important for receptor interaction have been identified from 1HWG. Thus, the selection of appropriate positions for introducing disulphide bonds, which are neutral with respect to biological activity, can be guided by analyzing the 1HWG structure.

The cysteine mutants may be chosen such that the introduced disulphide bonds provide increased stability towards proteolytic cleavage. The susceptibility of a protein to protease cleavage is defined in part by the primary amino acid sequence of said protein. Proteases may be relatively unspecific or may, with variable degree of selectivity, recognize specific motifs in the primary amino acid sequence. However, the three dimensional structure and dynamics of the protein molecule acting as a substrate strongly influence proteolytic stability. Highly flexible and dynamic loop structures are particularly vulnerable to protease catalyzed cleavage, whereas well structured regions are generally less so. Thus, protection against proteolytic cleavage can be obtained by stabilizing dynamic regions of a protein by introducing disulphide bonds.

One aspect of the invention relates to a growth hormone compound comprising additional disulfide bonds in SEQ ID No. 1. As described herein below the polypeptide of a growth hormone compound according to the invention preferably has a high level of identity to human growth hormone identified by SEQ ID No. 1 and accordingly a growth hormone compound comprises one or more additional disulfide bond(s) compared to human growth hormone as defined in SEQ ID No. 1.

Accordingly, one embodiment of present invention provides stable GH compounds according to SEQ ID No.1 made resistant to proteolytic degradation by introduction of additional disulphide bonds.

In one embodiment according to the invention a growth hormone compound comprises additional disulphide bonds between at least one of the amino acids pairs in the positions corresponding to R16C/L117C, A17C/E174C, H21C/M170C, D26/V102C, D26/Y103C, N47C/T50C, Q49C/G161C, F54C/Y143C, F54C/S144C, F54C/F146C, S55C/Y143C, S57C/Y143C, I58C/Q141C, I58C/Y143C, I58C/S144C, P59C/Q137C, P61C/E66C, P61C/T67C, S71C/S132C, L73C/S132C, L73C/F139C, R77C/I138C, R77C/F139C, L81C/Q141C, L81C/Y143C, Q84C/Y143C, Q84C/S144C, /S85C/Y143C, S85C/S144C, P89C/F146C, F92C/F146C, F92C/T148C, R94C/D107C, V102C/A105C, L156C/F146C, L156C/T148C and/or V185C/S188C in SEQ ID No. 1.

In one embodiment of the present invention a growth hormone compound comprises additional disulphide bonds between at least one of the amino acid pairs in the positions corresponding to, but not limited to R16C/L117C, A17C/E174C, H21C/M170C, N47C/T50C, Q49C/G161C, F54C/S144C, F54C/F146C, I58C/Q141C, I58C/S144C, P59C/Q137C, P61C/E66C, P61C/T67C, S71C/S132C, L73C/S132C, L73C/F139C, R77C/I138C, R77C/F139C, L81C/Q141C, L81C/Y143C, Q84C/Y143C, S85C/Y143C, P89C/F146C, F92C/F146C, F92C/T148C, R94C/D107C, V102C/A105C, L156C/F146C, L156C/T148C and/or V185C/S188C in SEQ ID No. 1.

In one embodiment of the present invention a growth hormone compound comprise additional disulphide bonds between at least one of the amino acid pairs in the positions corresponding to but not limited to A17C/E174C, H21C/M170C, S71C/S132C, Q84C/Y143C and R94C/D107C in SEQ ID No. 1.

In one embodiment of the present invention a growth hormone compound comprises an additional disulphide bond between the amino acid pair in the positions corresponding to Q84C/Y143C in SEQ ID No. 1.

In one embodiment according to the invention a growth hormone compound comprises at least one pair of mutations corresponding to R16C/L117C, A17C/E174C, H21C/M170C, D26/V102C, D26/Y103C, N47C/T50C, Q49C/G161C, F54C/Y143C, F54C/S144C, F54C/F146C, S55C/Y143C, S57C/Y143C, I58C/Q141C, I58C/Y143C, I58C/S144C, P59C/Q137C, P61C/E66C, P61C/T67C, S71C/S132C, L73C/S132C, L73C/F139C, R77C/I138C, R77C/F139C, L81C/Q141C, L81C/Y143C, Q84C/Y143C, Q84C/S144C, S85C/Y143C, S85C/S144C, P89C/F146C, F92C/F146C, F92C/T148C, R94C/D107C, V102C/A105C, L156C/F146C, L156C/T148C and/or V185C/S188C in SEQ ID No. 1.

In one embodiment of present invention growth hormone compound comprises at least one pair of mutations corresponding to, but not limited to R16C/L117C, A17C/E174C, H21C/M170C, N47C/T50C, Q49C/G161C, F54C/S144C, F54C/F146C, I58C/Q141C, I58C/S144C, P59C/Q137C, P61C/E66C, P61C/T67C, S71C/S132C, L73C/S132C, L73C/F139C, R77C/I138C, R77C/F139C, L81C/Q141C, L81C/Y143C, Q84C/Y143C, S85C/Y143C, P89C/F146C, F92C/F146C, F92C/T148C, R94C/D107C, V102C/A105C, L156C/F146C, L156C/T148C and/or V185C/S188C in SEQ ID No. 1.

In one embodiment of present invention growth hormone compound comprises at least one pair of mutations corresponding to, but not limited to A17C/E174C, H21C/M170C, S71C/S132C, Q84C/Y143C and R94C/D107C in SEQ ID No. 1.

In one embodiment of present invention growth hormone compound of the present invention comprises one pair of mutations corresponding to position Q84C/Y143C in SEQ ID No. 1.

In one embodiment of the present invention the proteolytic stability of growth hormone compound is achieved by introducing a disulphide bond between a loop segment and a helical structure.

In one embodiment of the present invention the proteolytic stability of growth hormone compound is achieved by introducing a disulphide bond within a loop segment.

In one embodiment of the present invention the proteolytic stability of growth hormone compound is achieved by introducing a disulphide bond between loop segments.

In one embodiment of the present invention the proteolytic stability of growth hormone compound is achieved by introducing a disulphide bond between helices.

In one embodiment of the present invention at least one of the introduced disulphide bonds links two cysteine residues of a growth hormone compound, wherein at least one of said cysteine residues is not present in wild type hGH.

In one embodiment of the present invention the introduced disulphide bonds of a growth hormone compound are positioned between cysteine residues that are selected using distance and geometry criteria described in Dombkowski A., A., Bioinformatics 19, 1852-1853 (2003) and Petersen et al., Protein Eng. 12(7), 535-548 (1999).

In one embodiment of the present invention the introduced disulphide bond(s) of the growth hormone compound stabilize the loop connecting H3 and H4 (L3, residues 128-154), i.e. at least one of the cysteines in the introduced disulphide bond is positioned in the segment comprising residues 128-154 (FIGS. 1 and 2).

TABLE 1

| | First Amino Acid as defined by sequence alignment with SEQ ID No. 1. | Second Amino Acid as defined by sequence alignment with SEQ ID No. 1. | Secondary Structural segments connected[a] |
|---|---|---|---|
| 1. | 16 | 117 | H1-H3 |
| 2. | 17 | 174 | H1-H4 |
| 3. | 21 | 170 | H1-H4 |
| 4. | 26 | 102 | H1-L2 |
| 5. | 26 | 103 | H1-L2 |
| 6. | 47 | 50 | L1-L1 |
| 7. | 49 | 161 | L1-L1 |
| 8. | 54 | 143 | L1-L3 |
| 9. | 54 | 144 | L1-L3 |
| 10. | 54 | 146 | L1-L3 |
| 11. | 55 | 143 | L1-L3 |
| 12. | 57 | 143 | L1-L3 |

TABLE 1-continued

| | First Amino Acid as defined by sequence alignment with SEQ ID No. 1. | Second Amino Acid as defined by sequence alignment with SEQ ID No. 1. | Secondary Structural segments connected[a] |
|---|---|---|---|
| 13. | 58 | 141 | L1-L3 |
| 14. | 58 | 143 | L1-L3 |
| 15. | 58 | 144 | L1-L3 |
| 16. | 59 | 137 | L1-L3 |
| 17. | 61 | 66 | L1-L1 |
| 18. | 61 | 67 | L1-L1 |
| 19. | 71 | 132 | L1-L3 |
| 20. | 73 | 132 | H2-L3 |
| 21. | 73 | 139 | H2-L3 |
| 22. | 77 | 138 | H2-L3 |
| 23. | 77 | 139 | H2-L3 |
| 24. | 81 | 141 | H2-L3 |
| 25. | 81 | 143 | H2-L3 |
| 26. | 84 | 143 | H2-L3 |
| 27. | 84 | 144 | H2-L3 |
| 28. | 85 | 143 | H2-L3 |
| 29. | 85 | 144 | H2-L3 |
| 30. | 89 | 146 | H2-L3 |
| 31. | 92 | 146 | H2-L3 |
| 32. | 92 | 148 | H2-L3 |
| 33. | 94 | 107 | H2-H3 |
| 34. | 102 | 105 | L2-H3 |
| 35. | 156 | 146 | H4-L3 |
| 36. | 156 | 148 | H4-L3 |
| 37. | 185 | 188 | Ct-Ct |

[a]H1-H4 refer to helix 1-4, L1-L3 refer to loops 1-3, and Ct refer to C-terminal segment.

As described above the invention relates to a growth hormone compound comprising an additional disulfide bond between a loop segment and a helical segment or within a loop segment or between loop segments or between helical segments of the polypeptide. The location of any such additional disulfide bond is for the purpose of this application described with reference to the polypeptide of hGH as defined in SEQ ID No. 1.

In one embodiment a growth hormone compound according to the invention comprises at least one pair of mutations corresponding to R16C/L117C, A17C/E174C, H21C/M170C, D26/V102C, D26/Y103C, N47C/T50C, Q49C/G161C, F54C/Y143C, F54C/S144C, F54C/F146C, S55C/Y143C, S57C/Y143C, I58C/Q141C, I58C/Y143C, I58C/S144C, P59C/Q137C, P61C/E66C, P61C/T67C, S71C/S132C, L73C/S132C, L73C/F139C, R77C/I138C, R77C/F139C, L81C/Q141C, L81C/Y143C, Q84C/Y143C, Q84C/S144C, S85C/Y143C, S85C/S144C, P89C/F146C, F92C/F146C, F92C/T148C, R94C/D107C, V102C/A105C, L156C/F146C, L156C/T148C and/or V185C/S188C in SEQ ID No. 1.

In one embodiment a growth hormone compound comprises at least one pair of mutations corresponding to A17C/E174C, H21C/M170C, D26/V102C, D26/Y103C, F54C/Y143C, F54C/S144C, F54C/F146C, S55C/Y143C, S57C/Y143C, I58C/Q141C, I58C/Y143C, I58C/S144C, P59C/Q137C, S71C/S132C, L81C/Y143C, Q84C/Y143C, S85C/Y143C, S85C/S144C, F92C/T148C and/or R94C/D107C in SEQ ID No. 1.

In one embodiment a growth hormone compound comprises at least one pair of mutations corresponding to A17C/E174C, H21C/M170C, F54C/S144C, F54C/F146C, I58C/Q141C, I58C/S144C, P59C/Q137C, S71C/S132C, L81C/Y143C, Q84C/Y143C, S85C/Y143C, F92C/T148C and/or R94C/D107C in SEQ ID No. 1.

One embodiment according to the invention relates to a growth hormone compound comprising an additional disulfide bond wherein at least one of the cysteines is present in L3 (AA 128-154 in SEQ ID NO 1), or such as in the middle region of the loop defined by AA 135-148) or corresponding amino acid residues.

In one embodiment a growth hormone compound at least one of the cysteines of the additional disulfide bond is present in L3, in a position corresponding to AA 141, AA142, AA143, AA144, AA145 or AA146, preferably AA143 or AA144 in SEQ ID No. 1.

In one embodiment a growth hormone compound comprises at least one pair of mutations corresponding to F54C/Y143C, F54C/S144C, F54C/F146C, S55C/Y143C, S57C/Y143C, I58C/Q141C, I58C/Y143C, I58C/S144C, P59C/Q137C, S71C/S132C, L73C/S132C, L73C/F139C, R77C/I138C, R77C/F139C, L81C/Q141C, L81C/Y143C, Q84C/Y143C, Q84C/S144C, S85C/Y143C, S85C/S144C, P89C/F146C, F92C/F146C and/or F92C/T148C in SEQ ID No. 1.

In one embodiment a growth hormone compound comprises at least one pair of mutations corresponding to F54C/Y143C, F54C/S144C, F54C/F146C, S55C/Y143C, S57C/Y143C, I58C/Q141C, I58C/Y143C, I58C/S144C, P59C/Q137C, S71C/S132C, L81C/Y143C, Q84C/Y143C, S85C/Y143C, S85C/S144C and/or F92C/T148C in SEQ ID No. 1.

In one embodiment a growth hormone compound comprises at least one pair of mutations corresponding to F54C/S144C, F54C/F146C, I58C/Q141C, I58C/S144C, P59C/Q137C, S71C/S132C, L81C/Y143C, Q84C/Y143C, S85C/Y143C and/or F92C/T148C in SEQ ID No. 1.

One embodiment according to the invention relates to a growth hormone compound comprising an additional disulfide bond connecting L3 with L1.

In one embodiment a growth hormone compound comprises an additional disulfide bond connecting an amino acid residue corresponding to AA54, AA55, AA56, AA57, AA58 or AA59 in L3 with an amino acid corresponding to AA143 or AA144 in L1 of SEQ ID No. 1.

In one embodiment a growth hormone compound according to the invention comprises at least one pair of mutations corresponding to F54C/Y143C, F54C/S144C, F54C/F146C, S55C/Y143C, S57C/Y143C, I58C/Q141C, I58C/Y143C, I58C/S144C, P59C/Q137C and/or S71C/S132C in SEQ ID No. 1.

In one embodiment a growth hormone comprises at least one pair of mutations corresponding to F54C/S144C, F54C/F146C, I58C/Q141C, I58C/S144C, P59C/Q137C and/or S71C/S132C in SEQ ID No. 1.

One embodiment according to the invention relates to a growth hormone compound comprising an additional disulfide bond connecting L3 with a helical segment, such as helix 2 (H2).

In one embodiment a growth hormone compound comprises an additional disulfide bond connecting an amino acid residue corresponding to AA84 or AA85 in H2 with an amino acid corresponding to AA143 or AA144 in L3 of SEQ ID No. 1.

In one embodiment a growth hormone compound comprises at least one pair of mutations corresponding to L73C/S132C, L73C/F139C, R77C/I138C, R77C/F139C, L81C/Q141C, L81C/Y143C, Q84C/Y143C, Q84C/S144C, S85C/Y143C, S85C/S144C, P89C/F146C, F92C/F146C and F92C/T148C in SEQ ID No.

In one embodiment a growth hormone compound comprises at least one pair of mutations corresponding to L81C/Y143C, Q84C/Y143C, S85C/Y143C, S85C/S144C and/or F92C/T148C in SEQ ID No. 1.

In one embodiment a growth hormone compound comprises at least one pair of mutations corresponding to L81C/Y143C, Q84C/Y143C, S85C/Y143C and/or F92C/T148C in SEQ ID No. 1.

One embodiment according to the invention relates to a growth hormone compound comprising an additional disulfide bond connecting L2 with helix 1.

In one embodiment a growth hormone compound comprises at least one pair of mutations corresponding to D26C/V102C or D26C/Y103C.

For disulphide bridges between two cysteine residues, the cysteine residues may be introduced or substituted in any of the regions or positions as defined hereinbefore in order to facilitate formation of one or more introduced disulphide bonds as required. Substitution and insertions of amino acid residues can be carried out by standard techniques known to a person skilled in the art.

According to the invention the one or more additional disulfide bond(s) is/are obtained by amino acid substitution of at least two amino acids compared SEQ ID No. 1. In a further embodiment the compound comprises exactly one additional disulfide bond compared to SEQ ID No. 1. In one embodiment the compound according to the invention comprises at least 2 amino acid substitutions compared to SEQ ID No. 1. In one further embodiment the compound comprises exactly 2 amino acid substitutions compared to SEQ ID No. 1. In one embodiment the polypeptide of a growth hormone compound according to the invention comprises at least two additional cysteines compared to human growth hormone as defined in SEQ ID No. 1. In a further embodiment the polypeptide comprises exactly two additional cysteines compared to human growth hormone as defined in SEQ ID No. 1.

In one embodiment of the present invention the growth hormone compound is chemically modified via attaching moieties such as, but not limited to, PEGs, carbohydrates, albumin binders, fatty acids, alkyl chains, lipophilic groups, vitamins, bile acids, or spacers to the side chains or main chain of the growth hormone compound in addition to comprising additional disulfide bonds.

In one embodiment of the present the growth hormone compound is chemically modified in order to facilitate transport across the epithelia when compared to hGH.

In one embodiment of the present invention a growth hormone compound of the present invention is chemically modified in order to obtain a prolonged duration of in vivo action.

In one embodiment of present invention a growth hormone compound is chemically modified in order to obtain a prolonged duration of functional in vivo half-life.

In one embodiment of present invention the chemical modifications of growth hormone compound may also be transient in nature, i.e. they may readily be removed in vivo.

In one embodiment of the present invention the growth hormone compound modifications can take place at any amino acid residue not interfering with binding of the growth hormone compound to the hGHR.

In one embodiment of the present invention a growth hormone compound has increased stability towards proteolytic cleavage.

In one embodiment of the present invention a growth hormone compound has increased stability towards proteolytic degradation by a pancreatic protease.

In one embodiment of the present invention a growth hormone compound has increased stability towards proteolytic degradation by proteases present in the gastrointestinal tract.

In one embodiment of the present invention a growth hormone compound has increased stability towards proteolytic degradation by proteases present in mammalian plasma.

One embodiment of the present invention relates to a growth hormone compound comprising one or more additional disulfide bond(s) which is stabilized towards degradation by protease(s), such as digestive proteases, such as pepsin, trypsin, chymotrypsin, carboxypeptidase and/or elastases.

In one embodiment of the present invention a growth hormone compound has increased stability towards proteolytic degradation by trypsin, chymotrypsin and/or elastase.

In one embodiment a growth hormone compound is stabilized towards degradation by chymotrypsin and/or elastase.

In one embodiment a growth hormone compound comprises at least one pair of mutations corresponding to H21/M170, D26/V102C, D26/Y103C, F54C/Y143C, F54C/S144C, S55C/Y143C, S57C/Y143C, I58C/Q141C, I58C/Y143C, I58C/S144C, P59C/Q137C, S71C/S132C, L81C/Y143C, Q84C/Y143C, S85C/Y143C and/or S85C/S144C in SEQ ID No. 1.

In one embodiment a growth hormone compound comprises at least one pair of mutations corresponding to H21/M170, F54C/S144C, S55C/Y143C, S57C/Y143C, I58C/Q141C, I58C/S144C, P59C/Q137C, S71C/S132C, L81C/Y143C, Q84C/Y143C and/or S85C/Y143C in SEQ ID No. 1.

In one embodiment a growth hormone compound comprises at least one pair of mutations corresponding to D26/V102C, D26/Y103C, S57C/Y143C, I58C/S144C, P59C/Q137C, S71C/S132C, Q84C/Y143C, S85C/Y143C, S85C/S144C, F92C/T148C and/or R94C/D107C in SEQ ID No. 1.

In one embodiment a growth hormone compound comprises at least one pair of mutations corresponding to I58C/S144C, P59C/Q137C, S71C/S132C, Q84C/Y143C, S85C/Y143C, F92C/T148C and/or R94C/D107C in SEQ ID No. 1.

In one embodiment a growth hormone compound comprises at least one pair of mutations corresponding to S57C/Y143C, Q84C/Y143C, S85C/Y143C and/or S85C/S144C in SEQ ID No. 1.

In one embodiment a growth hormone compound comprises at least one pair of mutations corresponding to Q84C/Y143C and/or S85C/Y143C in SEQ ID No. 1

In one embodiment of the present invention a growth hormone compound has increased in vivo half life.

In one embodiment of the present invention a growth hormone compound has increased shelf life.

In one embodiment of the present invention a growth hormone compound may be a fusion protein.

One embodiment of the present invention relates to a growth hormone compound, wherein the polypeptide sequence is at least 80%, such as 90% or such as 95% identical to hGH defined by SEQ ID No. 1. In further embodiments the polypeptide is 96%, 97%, 98%, or 99% identical to hGH defined by SEQ ID No. 1.

In one embodiment of the present invention a growth hormone compound is a polypeptide comprising an amino acid sequence having at least 20%, such as at least 30%, for instance at least 40%, such as at least 50%, for instance at least 60%, such as at least 70%, for instance at least 80%, such as at least 90% identity, for instance at least 95%, such as at least 96%, for instance at least 97%, such as at least 98%, for instance at least 99% identity to SEQ ID No. 1 and which polypeptide has an activity in the assay described in Example 3 and Example 3A (hypoxectomized rats) of at least 1%, such as at least 5%, for instance at least 10%, such as at least 25% of the activity of hGH. To avoid doubt, a growth hormone compound of the invention may also have a higher activity than hGH in these assays. If the growth hormone compound is derivatized in some way, the activity of the growth hormone in relation to hGH should be measured on the underivatized growth hormone compound, as the derivatization may change the activity significantly. For instance in the case of a growth hormone compound derivatized with a property-modifying group that prolongs the functional in vivo half-life of the growth hormone compound, the activity of the derivatized growth hormone compound may be much lower than the activity of hGH, which decrease is counteracting by the prolonged residence time. In one embodiment, the growth hormone compound is a fragment of such a polypeptide, which fragment has retained a significant amount of the growth hormone activity as described above.

In one embodiment of the present invention a growth hormone compound is a truncated version of hGH, i.e. one or more amino acid residues have been deleted from the N- and/or C-termini corresponding to SEQ No. 1 wherein the said compound retain desired biological properties of wild type hGH.

One embodiment of the present invention relates to a growth hormone compound comprising additional disulfide bonds in SEQ ID No. 1 or comprising one or more additional disulfide bond(s) compared to human growth hormone as defined in SEQ ID No. 1, wherein said compound has an in vitro activity which is comparable to the in vitro activity of hGH defined by SEQ ID No. 1. In vitro activity of growth hormone compounds is preferably measured in a BAF assay as described in Example 3 herein. In one embodiment a compound according to the invention may have an in vitro activity which is different from the in vitro activity of hGH. As described above a lower in vitro activity may be compensated by other in vivo functionalities. In an embodiment the in vitro activity may be such as at least 1%, such as at least 5%, for instance at least 10%, such as at least 25% of the activity of hGH. In a further embodiment the EC50 ratio for a compound relative to wild type hGH defined by SEQ ID No. 1 is not more that 10, not more than 8, not more than 6, not more than 4, not more than 2. In an embodiment the EC50 ratio for said compound compared to wild type hGH defined by SEQ ID No. 1 is from 5-0.01 or such as from 3-0.01 or such as is from 2-0.01. In an alternative the EC50 may according to the invention be measure by Surface Plasmon Resonance analysis (Biacore) as described in Example 4. In corresponding embodiments the in vitro activity determined by Biacore, may be such as at least 1%, such as at least 5%, for instance at least 10%, such as at least 25% of the activity of hGH. In further embodiments the EC50 ratio for a compound relative to wild type hGH defined by SEQ ID No. 1 determined by Biacore is not more that 10, not more than 8, not more than 6, not more than 4, not more than 2. In one embodiment the EC50 ratio for said compound compared to wild type hGH defined by SEQ ID No. 1 is from 5-0.01 or such as from 3-0.01 or such as 2-0.01.

Other examples of GH compounds into which additional disulphide bridges may be introduced include those disclosed in WO 92/09690 (Genentech), U.S. Pat. No. 6,004,931 (Genentech), U.S. Pat. No. 6,143,523 (Genentech), U.S. Pat. No. 6,136,536 (Genentech), U.S. Pat. No. 6,057,292 (Genentech), U.S. Pat. No. 5,849,535 (Genentech), WO 97/11178 (Genentech), WO 90/04788 (Genentech), WO 02/055532 (Maxygen APS and Maxygen Holdings), U.S. Pat. No. 5,951,972 (American Cynanamid Corporation), US 2003/0162949 (Bolder Biotechnologies, Inc.) which are incorporated herein by reference. Further included are natural variants of hGH, such as the 20 kDa described by Masuda, N et all, Biochim. Biophys. Acta 949 (1), 125-131 (1988.).

In all embodiments described herein it is a further option that the growth hormone compound has a Gly residue in a position corresponding to position 120 of SEQ ID No. 1.

In the present context, the words "human growth hormone (hGH)', "hGH wt" and "wild type hGH (wthGH)" are used interchangeably and refer both to a protein with an amino acid sequence as SEQ ID No.1.

In the present context, the terms "peptide" and "polypeptide" are used interchangeably and are intended to indicate the same. The terms "peptide" or "polypeptide" are intended to indicate a sequence of two or more amino acids joined by peptide bonds, wherein said amino acids may be natural or unnatural. The constituent amino acids may be from the group of the amino acids encoded by the genetic code and they may be natural amino acids which are not encoded by the genetic code, as well as synthetic amino acids. Natural amino acids which are not encoded by the genetic code are e.g. Hyp (hydroxy-proline), γ-carboxyglutamate, Orn (ornithine), phosphoserine, D-alanine and D-glutamine. Synthetic amino acids comprise amino acids manufactured by chemical synthesis, such as D-isomers of the amino acids encoded by the genetic code such as D-alanine and D-leucine, Aad (α-aminoadipic acid), Aib (α-aminoisobutyric acid), Abu (α-aminobutyric acid), Agl (α-amino-glycine), Asu (α-aminosuberic acid), Cha (β-cyclopentyl-alanine), Chg (cyclohexyl glycine), Dab (α,γ-diaminobutyric acid), Dap (α,β-diaminopropanic acid), Hcy (homocysteine), Hpr (homoproline), Nle (Norleucine), Phg (phenylglycine), Hph (homophenylalanine), 1Nal (β-(1-naphthyl-alanine), 2Nal (β-(2-naphthyl-alanine), 2 Pal (−(2-pyridyl)-alanine, 3 Pal (β-(3-pyridyl)-alanine), Pip (4-amino-piperidine-4-carboxylic acid), Pra (propargyl-glycine), Pyr (pyroglutamic acid), Gla (γ-carboxy-glutamic acid), Hci (homocitruline), Nva (norvaline), Tle (tert-butylglycine), β-alanine, 3-aminomethyl benzoic acid and anthranilic acid.

The term also encompasses the term "proteins", which may consists of one polypeptide chain, or two or more polypeptide chains held together by non-covalent or covalent interactions, such as for instance cysteine bridges.

It is to be understood that the term is also intended to include peptides, which have been derivatized, for instance by attaching moieties such as, but not limited to, PEG, carbohydrates, fatty acids, albumin binders, alkyl chains, lipophilic groups, vitamins, bile acids, or spacers to the side chains or main chain of the peptide in addition to comprising the additional disulfide bonds. The term peptide includes any suitable peptide and may be used synonymously with the terms polypeptide and protein, unless otherwise stated or contradicted by context, provided that the reader recognize that each type of respective amino acid polymer-containing molecule may be associated with significant differences and thereby form individual embodiments of the present invention (for example, a peptide such as an antibody, which is composed of multiple polypeptide chains, is significantly different from, for example, a single chain antibody, a peptide immunoadhesin, or single chain immunogenic peptide). Therefore, the term peptide herein should generally be understood as referring to any suitable peptide of any suitable size and composition (with respect to the number of amino acids and number of associated chains in a protein molecule). Moreover, peptides described herein may comprise non-naturally occurring and/or non-L amino acid residues, unless otherwise stated or contradicted by context.

The term peptide, unless otherwise stated or contradicted by context, (and if discussed as individual embodiments of the term(s) polypeptide and/or protein) also encompasses derivatized peptide molecules. A derivatized peptide molecules is one in which one or more of the amino acid residues of the peptide have been chemically modified (for instance by alkylation, acylation, ester formation, or amide formation) or associated with one or more non-amino acid organic and/or inorganic atomic or molecular substituents (for instance a polyethylene glycol (PEG) group, a lipophilic substituent (which optionally may be linked to the amino acid sequence of the peptide by a spacer residue or group such as β-alanine, γ-aminobutyric acid (GABA), L/D-glutamic acid, succinic acid, and the like), a fluorophore, biotin, a radionuclide, etc.) and may also or alternatively comprise non-essential, non-naturally occurring, and/or non-L amino acid residues, unless otherwise stated or contradicted by context (however, it should again be recognized that such derivatives may, in and of themselves, be considered independent features of the present invention and inclusion of such molecules within the meaning of peptide is done for the sake of convenience in describing the present invention rather than to imply any sort of equivalence between naked peptides and such derivatives).

Non-limiting examples of such amino acid residues include for instance 2-amino-adipic acid, 3-aminoadipic acid, β-alanine, β-aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2'-di-aminopimelic acid, 2,3-diaminopropionic acid, N-ethylglycine, N-ethylasparagine, hydroxy-lysine, allohydroxylysine, 3-hydroxyproline, 4-hydroxyproline, isodesmosine, alloisoleucine, N-methylglycine, N-methylisoleucine, 6-N-methyllysine, N-methylvaline, norvaline, norleucine, ornithine, propargyl-glycine and statine halogenated amino acids.

A "compound" described in the present invention may be a "protein" or "peptide" or "polypeptide" which may be an "analogue" or a "derivative" or a "variant", which retains desired biological activities similar to wthGH, irrespective to the manner it has been modified.

The term "analogue" or "variant" as used herein when referring to a polypeptide, means a modified version of said peptide wherein one or more amino acid residues of the peptide have been substituted by other amino acid residues and/or wherein one or more amino acid residues have been deleted from the peptide and or wherein one or more amino acid residues have been added to the peptide. Such substitution or addition or deletion of amino acid residues can take place at the N-terminal of the peptide and/or at the C-terminal of the peptide and/or in between N- or C-terminal of the peptide. All amino acids for which the optical isomer is not stated are to be understood to mean the L-isomer.

The terms "disulphide bond" or "disulphide bridge" are used interchangeably and intended to indicate the same. A "disulphide bond" or "disulphide bridge" in proteins is formed between the thiol groups of cysteine residues.

The term "additional cysteine" or "introduced cysteine" are used interchangeably and are intended to indicate the same. The terms are intended to include a cysteine residue not present in wild type hGH. To minimize structural changes the cysteine residue(s) are usually introduces by substitution of amino acid residue(s), whereby the length of hGH is maintained. Insertion of an additional cys residue may be tolerated in loop sections or at the boarders of the helixes, whereas introduction of cys residues within the helix'es is less attractive.

The term "additional disulphide bond" or "introduced disulphide bond" are used interchangeably and are intended to indicate the same. The terms are intended to include disulphide bonds formed between two cysteine residues of which at least one is not present in wild type hGH.

The term "derivative" as used herein refers to a peptide or polypeptide, wherein one or more amino acid residues of the peptide have been chemically modified by introduction of a polymer such as PEG, carbohydrate moieties, albumin binders, fatty acids, lipophilic groups, vitamins, bile acids or spacers to the side chains or main chain of the growth hormone compound. The chemical modifications may also be transient in nature, i.e. they may readily be removed in vivo. The chemical modifications can be post-translationally introduced, for instance by the cell itself or by chemical modifications performed on the peptide after expression.

The term "identity" as known in the art, refers to a relationship between the sequences of two or more peptides, as determined by comparing the sequences. In the art, "identity" also means the degree of sequence relatedness between peptides, as determined by the number of matches between strings of two or more amino acid residues. "Identity" measures the percent of identical matches between two or more sequences with gap alignments (if any) addressed by a particular mathematical model or computer program (i.e., "algorithms"). Identity of related peptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods to determine identity are designed to give the largest match between the sequences tested. Methods to determine identity are described in publicly available computer programs. Preferred computer program methods to determine identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

For example, using the computer algorithm GAP (Genetics Computer Group, University of Wisconsin, Madison, Wis.), two peptides for which the percent sequence identity is to be determined are aligned for optimal matching of their respective amino acids (the "matched span", as determined by the algorithm). A gap opening penalty (which is calculated as 3.times. the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al., Atlas of Protein Sequence and Structure, 5, (1978) for the PAM 250 comparison matrix; Henikoff et al., PNAS USA 89, 10915-10919 (1992) for the BLOSUM 62 comparison matrix) is also used by the algorithm.

Preferred parameters for a peptide sequence comparison include the following:

Algorithm: Needleman et al., J. Mol. Biol. 48, 443-453 (1970); Comparison matrix: BLOSUM 62 from Henikoff et al., PNAS USA 89, 10915-10919 (1992); Gap Penalty: 12, Gap Length Penalty: 4, Threshold of Similarity:

The GAP program is useful with the above parameters. The aforementioned parameters are the default parameters for peptide comparisons (along with no penalty for end gaps) using the GAP algorithm.

The terms "protease or proteases" is intended to include all enzymes possessing the ability to catalyze hydrolytic cleavage of a peptide bond. Proteases may be intra cellular, extra cellular or membrane bound proteases, proteinases or peptidases, and include proteases in the lumen of mammalian intestine and proteases present in mammalian plasma. Proteases may both be of the type endo proteases and exo proteases. Proteases may be of, but are not limited to, the following types: serine, cysteine, aspartic or metallo proteases. Specific examples of proteases are Trypsin, Chymotrypsin, Pepsin, Elastase, Factor VIIa, Factor Xa, Proteinase K, Carboxy peptidase, DPPIV, Neutral Endopeptidase, Granzyme B, Proline-endopeptidase, Staphylococcal peptidase I, Thermolysin, Thrombin, Arg-C proteinase, Asp-N endopeptidase, Caspase 1-10, Clostripain, Enterokinase, Glutamyl endopeptidase, Granzyme B, LysC, LysN, Proline-endopeptidase and Staphylococcal peptidase I.

The terms "resistant to proteolytic degradation" or "increased stability towards proteolytic degradation" or "increased stability towards proteolytic cleavage" or "improved proteolytic stability" or "proteolytic stability" are used interchangeably and intended to indicate the same. Used in connection to a hGH compound of the invention, the terms are intended to indicate that the polypeptide chain of said hGH compound is cleaved at a slower rate, compared to wild type hGH, by a protease under specific conditions.

The rate of proteolytic cleavage of a protein may be measure by several techniques known to the person skilled in the art. An example of an assay measuring the rate of degradation of hGH or a hGH compound is described in Example 5.

The invention also relates to methods useful for improving the pharmacological properties of hGH compounds. These pharmacological properties could for instance be an increase in the functional in vivo half-life, the plasma in vivo half-life, the mean residence time, a decrease in the renal clearance.

The term "functional in vivo half-life" is used in its normal meaning, i.e., the time at which 50% of the biological activity of the peptide, for instance a growth hormone compound, wherein the growth hormone compound is still present in the body/target organ, or the time at which the activity of the peptide, for instance growth hormone compound is 50% of its initial value. As an alternative to determining functional in vivo half-life, "in vivo plasma half-life", and protracted action may be determined, i.e., the time at which 50% of the peptide circulate in the bloodstream prior to being cleared. Determination of plasma half-life is often more simple than determining functional half-life and the magnitude of plasma half-life is usually a good indication of the magnitude of functional in vivo half-life.

The present invention is also directed towards pharmaceutical compositions comprising growth hormone compounds as defined and described herein.

In one embodiment, pharmaceutical compositions of the present invention may be administered in several dosage forms, for example, as solutions, suspensions, emulsions, microemulsions, multiple emulsion, foams, salves, pastes, plasters, ointments, tablets, coated tablets, tablets with co-formulation of absorption enhancing compounds, rinses, capsules, for example hard gelatine capsules and soft gelatine capsules, coated capsules, suppositories, drops, gels, sprays, powder, microparticles, nanoparticles, aerosols, inhalants, injection solution, in situ transforming solutions, for example in situ gelling, in situ setting, in situ precipitating, in situ crystallization, infusion solution, and implants.

In one embodiment of the present invention, the pharmaceutical compositions may be administered through oral, subcutaneous, intramuscular, nasal and i.v administration.

In one embodiment of the present invention, the oral pharmaceutical compositions may be administered through several routes of administration, for example, lingual, sublingual, buccal, in the mouth, in the stomach and intestine.

In one embodiment, pharmaceutical compositions of present invention are useful in the composition of solids, semisolids, powder and solutions for pulmonary administration of a peptide conjugate, such as e.g. a GH conjugate, using, for example a metered dose inhaler, dry powder inhaler and a nebulizer, all being devices well known to those skilled in the art.

In one embodiment, the pharmaceutical composition of the invention may further be compounded in, or attached to, for example through covalent, hydrophobic and electrostatic interactions, a drug carrier, drug delivery system and advanced drug delivery system in order to further enhance stability of the GH conjugate, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions thereof, well known to those skilled in the art of phase behavior in lipid-water systems, polymeric micelles, multiple emulsions, self-emulsifying, self-microemulsifying, cyclodextrins and derivatives thereof, and dendrimers.

The various examples of delivery systems for oral formulation incorporated herein by reference include non-ionic surfactants, which are known to increase the penetration of hydrophilic compounds. Examples of non-ionic surfactans are; sodium caprate, tartaric acid, Brij56, Brij58, Brij35, Brij30, fatty acid sugars, sodium taurodeoxycholate, sodium dodecyl sulfate, p-t-octyl phenol poloxyethylene-9.5 (Triton X-100) as described by Takatsuka et al., Eur. J. Pharm. Biopharm. 62, 52-58 (2006). The oral delivery system may also include protease inhibitors and mucolytic substances. Examples of protease inhibitors are soybean trypsin inhibitor, aprotinin and chymostatin. Examples of mucolytic substances are dithiotreitol and N-acetyl cysteine Enhancement of intestinal absorption of poorly absorbed hydrophilic compounds by simultaneous use of mycolytic agent and non-ionic surfactant. Also the 5-CNAC and similar compounds developed by Emisphere (WO2008101240, WO200811283687, WO2008027854, WO2008014430, US20080095837).

The oral formulation delivery systems may also include claudine modulators provide, which function as specific tight junction openers of epithelium cells. These claudine modulators function both transient or non-transient and interfere with the protein complexes that hold the epithelium cells tightly together tight junctions (Kondoh et al., Mol Pharmacology 67, 749-756 (2005)). Other examples of the delivery system for oral formulation include mucoadhesive agents, for example thiol containing additives (co-formulation) or covalently attached sidechains can increase the adhesion to the mucous layer, chitosan and carbomer molecules, polyacrylates, PEG and its derivatives, (Palmberger et al., Eur. J. Pharm. Biopharm. 66, 405-412 (2007); Leitner, V. M et al., Eur. J. Pharm. Biopharm. 56, 207-214 (2003); H. L. Leuβen et al., Parm. Res. 13, 1668-1672 (1996); H. L. Leuβen et al., Int. J. Pharmaceuticals 141, 39-52 (1996); Takatsuka et al., Eur. J. Pharm. Biopharm. 62, 52-58 (2006). Additional examples of delivery systems for oral formulation include cavelolar/Lipid rafts, SMVT (sodium dependent multi vitamin transporter). Another examples of formulations for oral delivery includes receptor-mediated trancytosis such as IRF (intrinsic factor receptor) using Vitamin B12 (Cobalamin) as substrate, FcRn (neonatal Fc receptor) and Transferrin. (M. Gumbleton, Adv. Drug. Del. Rev. 49, 281-300 (2001); K. C. Partlow et al., Biomaterials 29, 3367-3375 (2008); (Lee et al., Biotechnol. Appl. Biochem. 46, 211-217 (2007); S.Y. Chae et al., Bioconjugate Chem. 19, 334-341 (2008); Russell-Jones G.: Chapter 17 in Membrane Transporters as Drug Targets (1999); Said and Mohammed Curr. Opin. Gastroent. 22, 140-146 (2006); Chalasani et al., J. Con. Release 117, 421-429 (2007); H. L1 & Z. M. Qian Med. Res. Rev. 22, 225-250 (2002); Liang & Yang Biochem. Biophys. Res. Comm. 225, 734-738 (2005).

In one embodiment the GH compounds of the present invention exert growth hormone activity and may be used for treating diseases or states which will benefit from an increase in the amount of circulating growth hormone. Such diseases or states include growth hormone deficiency (GHD); Turner Syndrome; Prader-Willi syndrome (PWS); Noonan syndrome; Down syndrome; chronic renal disease, juvenile rheumatoid arthritis; cystic fibrosis, HIV-infection in children receiving HAART treatment (HIV/HALS children); short children born short for gestational age (SGA); short stature in children born with very low birth weight (VLBW) but SGA; skeletal dysplasia; hypochondroplasia; achondroplasia; idiopathic short stature (ISS); GHD in adults; fractures in or of long bones, such as tibia, fibula, femur, humerus, radius, ulna, clavicula, matacarpea, matatarsea, and digit; fractures in or of spongious bones, such as the scull, base of hand, and base of food; patients after tendon or ligament surgery in e.g. hand, knee, or shoulder; patients having or going through distraction oteogenesis; patients after hip or discus replacement, meniscus repair, spinal fusions or prosthesis fixation, such as in the knee, hip, shoulder, elbow, wrist or jaw; patients into which osteosynthesis material, such as nails, screws and plates, have been fixed; patients with non-union or mal-union of fractures; patients after osteatomia, e.g. from tibia or 1st toe; patients after graft implantation; articular cartilage degeneration in knee caused by trauma or arthritis; osteoporosis in patients with Turner syndrome; osteoporosis in men; adult patients in chronic dialysis (APCD); malnutritional associated cardiovascular disease in APCD; reversal of cachexia in APCD; cancer in APCD; chronic abstractive pulmonal disease in APCD; HIV in APCD; elderly with APCD; chronic liver disease in APCD, fatigue syndrome in APCD; Chron's disease; impaired liver function; males with HIV infections; short bowel syndrome; central obesity; HIV-associated lipodystrophy syndrome (HALS); male infertility; patients after major elective surgery, alcohol/drug detoxification or neurological trauma; aging; frail elderly; osteo-arthritis; traumatically damaged cartilage; erectile dysfunction; fibromyalgia; memory disorders; depression; traumatic brain injury; subarachnoid haemorrhage; very low birth weight; metabolic syndrome; glucocorticoid myopathy; or short stature due to glucocorticoid treatment in children. Growth hormones have also been used for acceleration of the healing of muscle tissue, nervous tissue or wounds; the acceleration or improvement of blood flow to damaged tissue; or the decrease of infection rate in damaged tissue.

In one embodiment, the present invention relates to a method of treating diseases, wherein growth hormone compound activity maybe used for treating diseases or states which will benefit from an increase in the amount of circulating growth hormone compound said method comprising administering to a patient an effective amount of a pharmaceutical composition of growth hormone compound or its conjugate of SEQ ID No.1.

In one embodiment, the present invention relates to a method comprising administration to a patient in need thereof an effective amount of a therapeutically effective amount of growth hormone compound according to the invention. The present invention thus provides a method for treating these diseases or states, the method comprising administering to a patient in need thereof a therapeutically effective amount of a growth hormone compound according to the present invention.

A "therapeutically effective amount" of a compound of the invention as used herein means an amount sufficient to cure, alleviate or partially arrest the clinical manifestations of a given disease and its complications. An amount adequate to accomplish this is defined as "therapeutically effective amount". Effective amounts for each purpose will depend on e.g. the severity of the disease or injury as well as the weight, sex, age and general state of the subject. It will be understood that determining an appropriate dosage may be achieved using routine experimentation, which is all within the ordinary skills of a trained physician or veterinary.

In one embodiment, the invention provides the use of a growth hormone compound or its conjugate in the manufacture of a medicament used in the treatment of the above mentioned diseases or states.

The growth hormone compounds as defined and described herein in the present invention are intended to be used as a therapeutic protein.

The production of polypeptides is well known in the art. For example, polypeptides may be produced by classical peptide synthesis, e.g. solid phase peptide synthesis using tert-Boc or Fmoc chemistry or other well established techniques, see e.g. Greene and Wuts, "Protective Groups in Organic Synthesis", John Wiley & Sons, 2006.

The polypeptides may also be produced by a method which comprises culturing a host cell containing a DNA sequence encoding the polypeptide and capable of expressing the polypeptide in a suitable nutrient medium under conditions permitting the expression of the peptide. For polypeptides comprising non-natural amino acid residues, the recombinant cell should be modified such that the non-natural amino acids are incorporated into the polypeptide, for instance by use of tRNA mutants.

The polypeptides may also be produced using cell-free in vitro transcription/translation systems. A polypeptide containing novel unnatural amino acids may also be produced using frameshift or nonsense suppression systems e.g. as described in J. Am. Chem. Soc. 125, 11782-11783 (2003), Science 301, 964-967 (2003), Science 292, 498-500 (2001), Science 303, 371-373 (2004) and references herein.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including separating the host cells from the medium by centrifugation or filtration. For extra cellular products the proteinaceous components of the supernatant are isolated by filtration, column chromatography or precipitation, e.g. microfiltration, ultrafiltration, isoelectric precipitation, purification by a variety of chromatographic procedures, e.g. ion exchange chromatography, hydrophobic interaction chromatography, gel filtration chromatography, affinity chromatography, or the like, dependent on the type of polypeptide in question. For intracellular or periplasmic products the cells isolated from the culture medium are disintegrated or permeabilised and extracted to recover the product polypeptide or precursor thereof.

The DNA sequence encoding the polypeptide may suitably be of genomic or cDNA origin, for instance obtained by preparing a genomic or cDNA library and screening for DNA sequences coding for all or part of the peptide by hybridisation using specific DNA or RNA probes in accordance with standard techniques (see, for example, Sambrook, J, Fritsch, E F and Maniatis, T, Molecular Cloning: A Laboratory Manual, Cold Spring Harbor Laboratory Press, New York, 1989). The DNA sequence encoding the polypeptide may also be prepared synthetically by established standard methods, e.g. the phosphoamidite method described by Beaucage and Caruthers, Tetrahedron Letters 22, 1859-1869 (1981), or the method described by Matthes et al., EMBO Journal 3, 801-805 (1984). The DNA sequence may also be prepared by polymerase chain reaction using specific primers, for instance as described in U.S. Pat. No. 4,683,202 or Saiki et al., Science 239, 487-491 (1988).

The DNA sequence encoding the peptide to be expressed may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extra-chromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector may be an expression vector in which the DNA sequence encoding the polypeptide is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the peptide to be expressed in a variety of host cells are well known in the art, cf. for instance Sambrook et al., supra.

The DNA sequence encoding the peptide to be expressed may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, for instance a gene the product of which complements a defect in the host cell or one which confers resistance to a drug, for instance ampicillin, kanamycin, tetracyclin, chloramphenicol, neomycin, hygromycin or methotrexate. For large scale manufacture the selectable marker may for instance not be antibiotic resistance, e.g. antibiotic resistance genes in the vector may be excised when the vector is used for large scale manufacture. Methods for eliminating antibiotic resistance genes from vectors are known in the art, see e.g. U.S. Pat. No. 6,358,705 which is incorporated herein by reference.

To direct the peptide to be expressed into the secretory pathway of the host cells, a secretory signal sequence (also known as a leader sequence, prepro-sequence or pre-sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

The procedures used to ligate the DNA sequences coding for the peptide to be expressed, the promoter and optionally the terminator and/or secretory signal sequence, respectively, and to insert them into suitable vectors containing the information necessary for replication, are well known to persons skilled in the art (cf., for instance, Sambrook et al., supra).

The host cell into which a DNA sequence or recombinant vector is introduced may be any cell which is capable of producing the present peptide and includes bacteria, yeast, fungi and higher eukaryotic cells. Examples of suitable host cells well known and used in the art are, without limitation, *E. coli, Saccharomyces cerevisiae*, or mammalian BHK or CHO cell lines. The peptide to be expressed can also be produced by using in vitro transcription/translation systems commonly known in the art.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law The invention as described herein is, without limitation hereto, further described by the following embodiments.

Embodiment 1

A growth hormone compound comprising additional disulfide bonds in SEQ ID No. 1.

Embodiment 2

A growth hormone compound according to embodiment 1, comprising additional disulfide bonds between at least one of the amino acid pairs in the positions corresponding to R16C/L117C, A17C/E174C, H21C/M170C, N47C/T50C, Q49C/G161C, F54C/S144C, F54C/F146C, I58C/Q141C, I58C/S144C, P59C/Q137C, P61C/E66C, P61C/T67C, S71C/

S132C, L73C/S132C, L73C/F139C, R77C/I138C, R77C/ F139C, L81C/Q141C, L81C/Y143C, Q84C/Y143C, S85C/ Y143C, P89C/F146C, F92C/F146C, F92C/T148C, R94C/ D107C, V102C/A105C, L156C/F146C, L156C/T148C and/ or V185C/S188C in SEQ ID No. 1.

Embodiment 3

A growth hormone compound according to embodiment 2, wherein the growth hormone compound comprises additional disulfide bonds between at least one of the amino acid pairs in the positions corresponding to A17C/E174C, H21C/M170C, Q84C/Y143C, S71C/S132C and/or R94C/D107C in SEQ ID No. 1.

Embodiment 4

A growth hormone compound according to embodiment 1, wherein the growth hormone compound comprises at least one pair of mutations corresponding to R16C/L117C, A17C/ E174C, H21C/M170C, N47C/T50C, Q49C/G161C, F54C/ S144C, F54C/F146C, I58C/Q141C, I58C/S144C, P59C/ Q137C, P61C/E66C, P61C/T67C, S71C/S132C, L73C/ S132C, L73C/F139C, R77C/I138C, R77C/F139C, L81C/ Q141C, L81C/Y143C, Q84C/Y143C, S85C/Y143C, P89C/ F146C, F92C/F146C, F92C/T148C, R94C/D107C, V102C/ A105C, L156C/F146C, L156C/T148C and/or V185C/S188C in SEQ ID No. 1.

Embodiment 5

A growth hormone compound according to embodiment 4, wherein the growth hormone compound comprises at least one pair of mutations corresponding to A17C/E174C, H21C/ M170C, S71C/S132C, Q84C/Y143C, and R94C/D107C in SEQ ID No. 1.

Embodiment 6

A growth hormone compound comprising one or more additional disulfide bond(s) compared to human growth hormone as defined in SEQ ID No. 1.

Embodiment 7

A growth hormone compound according to any of the previous embodiments, wherein the growth hormone compound comprises an additional disulfide bond between a loop segment and a helical segment or within a loop segment or between loop segments or between helical segments.

Embodiment 8

A growth hormone compound according to embodiment 6 or 7, wherein the compound comprises at least one pair of mutations corresponding to R16C/L117C, A17C/E174C, H21C/M170C, D26/V102C, D26/Y103C, N47C/T50C, Q49C/G161C, F54C/Y143C, F54C/S144C, F54C/F146C, S55C/Y143C, S57C/Y143C, I58C/Q141C, I58C/Y143C, I58C/S144C, P59C/Q137C, P61C/E66C, P61C/T67C, S71C/S132C, L73C/S132C, L73C/F139C, R77C/I138C, R77C/F139C, L81C/Q141C, L81C/Y143C, Q84C/Y143C, Q84C/S144C, S85C/Y143C, S85C/S144C, P89C/F146C, F92C/F146C, F92C/T148C, R94C/D107C, V102C/A105C, L156C/F146C, L156C/T148C and/or V185C/S188C in SEQ ID No. 1.

Embodiment 9

A growth hormone compound according to embodiment 8, wherein the compound comprises at least one pair of mutations corresponding to A17C/E174C, H21C/M170C, D26/ V102C, D26/Y103C, F54C/Y143C, F54C/S144C, F54C/ F146C, S55C/Y143C, S57C/Y143C, I58C/Q141C, I58C/ Y143C, I58C/S144C, P59C/Q137C, S71C/S132C, L81C/ Y143C, Q84C/Y143C, S85C/Y143C, S85C/S144C, F92C/ T148C and/or R94C/D107C in SEQ ID No. 1.

Embodiment 10

A growth hormone compound according to embodiment 9, wherein the compound comprises at least one pair of mutations corresponding to A17C/E174C, H21C/M170C, F54C/ S144C, F54C/F146C, I58C/Q141C, I58C/S144C, P59C/ Q137C, S71C/S132C, L81C/Y143C, Q84C/Y143C, S85C/ Y143C, F92C/T148C and/or R94C/D107C in SEQ ID No. 1.

Embodiment 11

A growth hormone compound according to any of the previous embodiments, wherein the growth hormone compound comprises an additional disulfide bond wherein at least one of the cysteines is present in L3 corresponding to AA 128-154 in SEQ ID NO 1 or such as in a region corresponding to AA 135-148 in SEQ ID No. 1.

Embodiment 12

A growth hormone compound according to embodiment 11, wherein at least one of the cysteines of the additional disulfide bond is present in L3 in a position corresponding to AA 141, AA142, AA143, AA144, AA145 or AA146, preferably AA143 or AA144 in SEQ ID No. 1.

Embodiment 13

A growth hormone compound according to embodiment 12, wherein the compound comprises at least one pair of mutations corresponding to F54C/Y143C, F54C/S144C, F54C/F146C, S55C/Y143C, S57C/Y143C, I58C/Q141C, I58C/Y143C, I58C/S144C, P59C/Q137C, S71C/S132C, L73C/S132C, L73C/F139C, R77C/I138C, R77C/F139C, L81C/Q141C, L81C/Y143C, Q84C/Y143C, Q84C/S144C, S85C/Y143C, S85C/S144C, P89C/F146C, F92C/F146C and/or F92C/T148C in SEQ ID No. 1.

Embodiment 14

A growth hormone compound according to embodiment 13, wherein the compound comprises at least one pair of mutations corresponding to F54C/Y143C, F54C/S144C, F54C/F146C, S55C/Y143C, S57C/Y143C, I58C/Q141C, I58C/Y143C, I58C/S144C, P59C/Q137C, S71C/S132C, L81C/Y143C, Q84C/Y143C, S85C/Y143C, S85C/S144C and/or F92C/T148C in SEQ ID No. 1.

Embodiment 15

A growth hormone compound according to embodiment 14, wherein the compound comprises at least one pair of mutations corresponding to F54C/S144C, F54C/F146C, I58C/Q141C, I58C/S144C, P59C/Q137C, S71C/S132C, L81C/Y143C, Q84C/Y143C, S85C/Y143C and/or F92C/ T148C in SEQ ID No. 1.

Embodiment 16

A growth hormone compound according to any of the previous claims, wherein the growth hormone compound comprises an additional disulfide bond connecting L3 with L1.

Embodiment 17

A growth hormone compound according to embodiment 16, wherein the compound comprises an additional disulfide bond connecting an amino acid residue corresponding to AA54, AA55, AA56, AA57, AA58 or AA59 in L3 with an amino acid corresponding to AA143 or AA144 in L1 of SEQ ID No. 1.

Embodiment 18

A growth hormone compound according to embodiment 16, wherein the compound comprises at least one pair of mutations corresponding to F54C/Y143C, F54C/S144C, F54C/F146C, S55C/Y143C, S57C/Y143C, I58C/Q141C, I58C/Y143C, I58C/S144C, P59C/Q137C and/or S71C/S132C in SEQ ID No. 1.

Embodiment 19

A growth hormone compound according to embodiment 18, wherein the compound comprises at least one pair of mutations corresponding to F54C/S144C, F54C/F146C, I58C/Q141C, I58C/S144C, P59C/Q137C and/or S71C/S132C in SEQ ID No. 1.

Embodiment 20

A growth hormone compound according to any of embodiments 1-15, wherein the growth hormone compound comprises an additional disulfide bond connecting L3 with a helical segment.

Embodiment 21

A growth hormone compound according to embodiment 20, wherein the growth hormone compound comprises an additional disulfide bond connecting L3 with helix 2.

Embodiment 22

A growth hormone compound according to embodiment 21, wherein the compound comprises an additional disulfide bond connecting an amino acid residue corresponding to AA84 or AA85 in H2 with an amino acid corresponding to AA143 or AA144 in L3 of SEQ ID No. 1.

Embodiment 23

A growth hormone compound according to embodiment 21, wherein the compound comprises at least one pair of mutations corresponding to L73C/S132C, L73C/F139C, R77C/I138C, R77C/F139C, L81C/Q141C, L81C/Y143C, Q84C/Y143C, Q84C/S144C, S85C/Y143C, S85C/S144C, P89C/F146C, F92C/F146C and F92C/T148C in SEQ ID No.1.

Embodiment 24

A growth hormone compound according to embodiment 23, wherein the compound comprises at least one pair of mutations corresponding to L81C/Y143C, Q84C/Y143C, S85C/Y143C, S85C/S144C and/or F92C/T148C in SEQ ID No. 1.

Embodiment 25

A growth hormone compound according to embodiment 24, wherein the compound comprises at least one pair of mutations corresponding to L81C/Y143C, Q84C/Y143C, S85C/Y143C and/or F92C/T148C in SEQ ID No. 1.

Embodiment 26

A growth hormone compound according to any of embodiments 1-10, wherein the growth hormone compound comprises an additional disulfide bond connecting L2 with helix 1.

Embodiment 27

A growth hormone compound according to embodiment 26, wherein the compound comprises at least one pair of mutations corresponding to D26C/V102C or D26C/Y103C.

Embodiment 28

A growth hormone compound according to any of the preceding embodiments, wherein the polypeptide sequence is at least 80%, such as 90%, such as 95%, such as 96%, such as 97%, such as 98% or such as 99% identical to hGH defined by SEQ ID No. 1.

Embodiment 29

A growth hormone compound according to any of the preceding embodiments, wherein the in vitro activity for said compound is at least 5% if the activity of wild type hGH defined by SEQ ID No. 1.

Embodiment 30

A growth hormone compound according to any of the previous embodiments, wherein the functional in vivo half-life of the polypeptide is 2 times or more compared to human growth hormone.

Embodiment 31

A growth hormone compound according to any of the previous embodiments, wherein the functional in vivo half-life of the polypeptide is between 2 and 10 times more compared to human growth hormone.

Embodiment 32

A growth hormone compound according to any of the preceding embodiments, wherein the growth hormone compound is stabilized towards degradation by protease(s), such as digestive proteases, such as pepsin, trypsin, chymotrypsin, carboxypeptidase and/or elastases.

Embodiment 33

A growth hormone compound according to embodiment 32, wherein the compound is stabilized towards degradation by Chymotrypsin and/or Elastase.

Embodiment 34

A growth hormone compound according to embodiment 33, wherein the compound comprises at least one pair of mutations corresponding to H21/M170, D26/V102C, D26/Y103C, F54C/Y143C, F54C/S144C, S55C/Y143C, S57C/Y143C, I58C/Q141C, I58C/Y143C, I58C/S144C, P59C/Q137C, S71C/S132C, L81C/Y143C, Q84C/Y143C, S85C/Y143C and/or S85C/S144C in SEQ ID No. 1.

Embodiment 35

A growth hormone compound according to embodiment 33, wherein the compound comprises at least one pair of mutations corresponding to H21/M170, F54C/S144C, S55C/Y143C, S57C/Y143C, I58C/Q141C, I58C/S144C, P59C/Q137C, S71C/S132C, L81C/Y143C, Q84C/Y143C and/or S85C/Y143C in SEQ ID No. 1.

Embodiment 36

A growth hormone compound according to embodiment 33, wherein the compound comprises at least one pair of mutations corresponding to D26/V102C, D26/Y103C, S57C/Y143C, I58C/S144C, P59C/Q137C, S71C/S132C, Q84C/Y143C, S85C/Y143C, S85C/S144C, F92C/T148C and/or R94C/D107C in SEQ ID No. 1.

Embodiment 37

A growth hormone compound according to embodiment 33, wherein the compound comprises at least one pair of mutations corresponding to I58C/S144C, P59C/Q137C, S71C/S132C, Q84C/Y143C, S85C/Y143C, F92C/T148C and/or R94C/D107C in SEQ ID No. 1.

Embodiment 38

A growth hormone compound according to embodiment 33, wherein the compound comprises at least one pair of mutations corresponding to S57C/Y143C, Q84C/Y143C, S85C/Y143C and/or S85C/S144C in SEQ ID No. 1.

Embodiment 39

A growth hormone compound according to embodiment 33, wherein the compound comprises at least one pair of mutations corresponding to Q84C/Y143C and/or S85C/Y143C in SEQ ID No. 1.

Embodiment 40

A growth hormone compound according to any of the previous embodiments, wherein the one or more additional disulfide bond(s) is/are obtained by amino acid substitution of at least two amino acid compared SEQ ID No. 1.

Embodiment 41

A growth hormone compound according to any of the previous embodiments wherein the compound comprises exactly one additional disulfide bond compared to SEQ ID No. 1.

Embodiment 42

A growth hormone compound according to any of the previous embodiments wherein the compound comprises exactly 2 amino acid substitutions compared to SEQ ID No. 1.

Embodiment 43

A growth hormone compound according to any of the previous embodiments comprising at least two additional cysteines compared to human growth hormone as defined in SEQ ID No. 1.

Embodiment 44

A growth hormone compound according to any of the previous embodiments comprising exactly two additional cysteines compared to human growth hormone as defined in SEQ ID No. 1.

Embodiment 45

A growth hormone compound according to any of the preceding embodiments, wherein the growth hormone compound is chemically modified by PEGylation, by attaching polymers, such as, but not limited to, sugar moieties, fatty acids, lipophilic groups, albumin binders, vitamins, bile acids, spacers to the side chains or main chain of the peptide.

Embodiment 46

A growth hormone compound according to embodiment 45, wherein chemical modification of growth hormone compound is transient in nature, i.e. they may readily be removed in vivo.

Embodiment 47

A growth hormone compound according to any of embodiments 45-46, wherein chemical modifications of amino acid residues can take place at the N-terminal of the peptide, at the C-terminal of the peptide and/or between the N- and C-terminal of the peptide.

Embodiment 48

A growth hormone compound according to any of embodiments 45-47, wherein the chemical modification takes place at amino acid residues Phe1, Gln40, Gln141 or Phe191.

Embodiment 49

A growth hormone compound according to any of embodiments 45-48, wherein the chemical modification is by PEG and wherein PEG is between 500 Da and 50 kDa.

Embodiment 50

A growth hormone compound according to any of embodiments 1-49, wherein the growth hormone compound is chemically modified in order to facilitate transport across the epithelia.

Embodiment 51

A growth hormone compound according to any of embodiments 1-49, wherein the growth hormone compound is chemically modified in order to facilitate transport across the epithelia when compared to wthGH.

Embodiment 52

A growth hormone compound according to any of embodiments 1-49, wherein the growth hormone compound is chemically modified in order to obtain a prolonged functional in vivo half-life when compared to wthGH.

Embodiment 53

A growth hormone compound according to embodiment 52, wherein the functional in vivo half-life of said growth hormone compound is 2 times or more compared to hGH.

Embodiment 54

A growth hormone compound according to embodiment 53, wherein the functional in vivo half-life is between 2 and 10 times compared to hGH.

Embodiment 55

A growth hormone compound according to any embodiments 45-49, wherein the chemical modification takes place at amino acid residues not interfering with binding of the growth hormone compound to the hGHR.

Embodiment 56

A growth hormone compound according to any of embodiments 49-55, wherein the growth hormone compound is stabilized towards proteolytic degradation by protease(s), such as as digestive proteases, such as pepsin, trypsin, chymotrypsin, carboxypeptidase and/or elastases.

Embodiment 57

A method for preparing a growth hormone compound with increased stability towards proteolytic degradation, which method comprises a step of
a. introducing additional disulfide bonds in hGH Embodiment 58

A method for preparing a growth hormone compound with increased stability towards proteolytic degradation according to any of embodiments 1-14, which method comprises a step of
a. introducing additional disulfide bonds in hGH by substituting one or more amino acid residues in hGH with one or more cysteine.

Embodiment 59

A method for preparing a growth hormone compound with increased stability towards proteolytic degradation according to embodiments 1-14, which comprises steps of
a. introducing additional disulfide bonds in hGH by adding one or more cysteine residues.

Embodiment 60

A pharmaceutical composition comprising growth hormone compound according to any of embodiments 1 to 56 and a pharmaceutically acceptable carrier/s.

Embodiment 61

A pharmaceutical composition according to embodiment 60, wherein said composition can be administered through lingual, sublingual, buccal, in the mouth, oral, in the stomach and intestine, nasal, pulmonary, epidermal, dermal, transdermal, and parenteral to patients.

Embodiment 62

A pharmaceutical composition according to embodiment 60 or 61, wherein said composition is orally administered composition.

Embodiment 63

A method of preparing a pharmaceutical composition wherein said composition comprising of growth hormone compound according to any of embodiments 1 to 56 and a pharmaceutically acceptable carrier/s.

Embodiment 64

A method of treating diseases wherein growth hormone activity may be used for treating diseases or states which will benefit from an increase in the amount of circulating growth hormone compound said method comprising administering to patient an effective amount of a growth hormone compound according to any of embodiments 1 to 56 or a pharmaceutical composition according to any of embodiments 6062.

Embodiment 65

A method of treating diseases according to embodiments 63 or 64, wherein disease is selected from growth hormone deficiency (GHD); Turner Syndrome; Prader-Willi syndrome (PWS); Noonan syndrome; Down syndrome; chronic renal disease, juvenile rheumatoid arthritis; cystic fibrosis, HIV-infection in children receiving HAART treatment (HIV/HALS children); short children born short for gestational age (SGA); short stature in children born with very low birth weight (VLBW) but SGA; skeletal dysplasia; hypochondroplasia; achondroplasia; idiopathic short stature (ISS); GHD in adults; fractures in or of long bones, such as tibia, fibula, femur, humerus, radius, ulna, clavicula, matacarpea, matatarsea, and digit; fractures in or of spongious bones, such as the scull, base of hand, and base of food; patients after tendon or ligament surgery in e.g. hand, knee, or shoulder; patients having or going through distraction oteogenesis; patients after hip or discus replacement, meniscus repair, spinal fusions or prosthesis fixation, such as in the knee, hip, shoulder, elbow, wrist or jaw; patients into which osteosynthesis material, such as nails, screws and plates, have been fixed; patients with non-union or mal-union of fractures; patients after osteatomia, e.g. from tibia or 1st toe; patients after graft implantation; articular cartilage degeneration in knee caused by trauma or arthritis; osteoporosis in patients with Turner syndrome; osteoporosis in men; adult patients in chronic dialysis (APCD); malnutritional associated cardiovascular disease in APCD; reversal of cachexia in APCD; cancer in APCD; chronic abstractive pulmonal disease in APCD; HIV in APCD; elderly with APCD; chronic liver disease in APCD, fatigue syndrome in APCD; Chron's disease; impaired liver function; males with HIV infections; short bowel syndrome; central obesity; HIV-associated lipodystrophy syndrome (HALS); male infertility; patients after major elective surgery, alcohol/drug detoxification or neurological trauma; aging; frail elderly; osteo-arthritis; traumatically damaged cartilage; erectile dysfunction; fibromyalgia; memory disorders; depression; traumatic brain injury; subarachnoid haemorrhage; very low birth weight; metabolic syndrome; glucocorticoid myopathy; or short stature due to glucocorticoid treatment in children.

Embodiment 66

A growth hormone according to any of embodiments 1 to 56 for use as an medicament

Embodiment 67

Use of a growth hormone according to any of embodiments 1 to 56 as an medicament.

Embodiment 68

Use of growth hormone compound according to any of embodiments 1 to 56 in treatment of disease.

Embodiment 69

Use according to embodiment 67 or embodiment 68, wherein disease is selected from growth hormone deficiency (GHD); Turner Syndrome; Prader-Willi syndrome (PWS); Noonan syndrome; Down syndrome; chronic renal disease, juvenile rheumatoid arthritis; cystic fibrosis, HIV-infection in children receiving HAART treatment (HIV/HALS children); short children born short for gestational age (SGA); short stature in children born with very low birth weight (VLBW) but SGA; skeletal dysplasia; hypochondroplasia; achondroplasia; idiopathic short stature (ISS); GHD in adults; fractures in or of long bones, such as tibia, fibula, femur, humerus, radius, ulna, clavicula, matacarpea, matatarsea, and digit; fractures in or of spongious bones, such as the scull, base of hand, and base of food; patients after tendon or ligament surgery in e.g. hand, knee, or shoulder; patients having or going through distraction oteogenesis; patients after hip or discus replacement, meniscus repair, spinal fusions or prosthesis fixation, such as in the knee, hip, shoulder, elbow, wrist or jaw; patients into which osteosynthesis material, such as nails, screws and plates, have been fixed; patients with non-union or mal-union of fractures; patients after osteatomia, e.g. from tibia or 1st toe; patients after graft implantation; articular cartilage degeneration in knee caused by trauma or arthritis; osteoporosis in patients with Turner syndrome; osteoporosis in men; adult patients in chronic dialysis (APCD); malnutritional associated cardiovascular disease in APCD; reversal of cachexia in APCD; cancer in APCD; chronic abstractive pulmonal disease in APCD; HIV in APCD; elderly with APCD; chronic liver disease in APCD, fatigue syndrome in APCD; Chron's disease; impaired liver function; males with HIV infections; short bowel syndrome; central obesity; HIV-associated lipodystrophy syndrome (HALS); male infertility; patients after major elective surgery, alcohol/drug detoxification or neurological trauma; aging; frail elderly; osteo-arthritis; traumatically damaged cartilage; erectile dysfunction; fibromyalgia; memory disorders; depression; traumatic brain injury; subarachnoid haemorrhage; very low birth weight; metabolic syndrome; glucocorticoid myopathy; or short stature due to glucocorticoid treatment in children.

Embodiment 70

Use of growth hormone compound according to any of embodiments 1 to 56 in manufacture of a medicament to be used in treatment of growth hormone deficiency (GHD); Turner Syndrome; Prader-Willi syndrome (PWS); Noonan syndrome; Down syndrome; chronic renal disease, juvenile rheumatoid arthritis; cystic fibrosis, HIV-infection in children receiving HAART treatment (HIV/HALS children); short children born short for gestational age (SGA); short stature in children born with very low birth weight (VLBW) but SGA; skeletal dysplasia; hypochondroplasia; achondroplasia; idiopathic short stature (ISS); GHD in adults; fractures in or of long bones, such as tibia, fibula, femur, humerus, radius, ulna, clavicula, matacarpea, matatarsea, and digit; fractures in or of spongious bones, such as the scull, base of hand, and base of food; patients after tendon or ligament surgery in e.g. hand, knee, or shoulder; patients having or going through distraction oteogenesis; patients after hip or discus replacement, meniscus repair, spinal fusions or prosthesis fixation, such as in the knee, hip, shoulder, elbow, wrist or jaw; patients into which osteosynthesis material, such as nails, screws and plates, have been fixed; patients with non-union or mal-union of fractures; patients after osteatomia, e.g. from tibia or 1st toe; patients after graft implantation; articular cartilage degeneration in knee caused by trauma or arthritis; osteoporosis in patients with Turner syndrome; osteoporosis in men; adult patients in chronic dialysis (APCD); malnutritional associated cardiovascular disease in APCD; reversal of cachexia in APCD; cancer in APCD; chronic abstractive pulmonal disease in APCD; HIV in APCD; elderly with APCD; chronic liver disease in APCD, fatigue syndrome in APCD; Chron's disease; impaired liver function; males with HIV infections; short bowel syndrome; central obesity; HIV-associated lipodystrophy syndrome (HALS); male infertility; patients after major elective surgery, alcohol/drug detoxification or neurological trauma; aging; frail elderly; osteo-arthritis; traumatically damaged cartilage; erectile dysfunction; fibromyalgia; memory disorders; depression; traumatic brain injury; subarachnoid haemorrhage; very low birth weight; metabolic syndrome; glucocorticoid myopathy; or short stature due to glucocorticoid treatment in children.

EXAMPLES

The invention will be further defined by reference to the following examples, which describe the preparation and characterization of the various compounds described herein and methods for assaying their biological activity. It will be apparent to those skilled in the art that many modifications, both to the materials and methods may be practiced without departing from the scope of the invention.

The TGase used in the examples is microbial transglutaminase from *Streptoverticillium mobaraense* according to U.S. Pat. No. 5,156,956.

Example 1

General Method for Preparing a hGH Compounds

The gene coding for the growth hormone compound was inserted recombinantly into a plasmid vector. Cysteine mutations were introduced by using QuikChange site-directed mutagenesis kit (Stratagene). A suitable *E. coli* strain was subsequently transformed using the plasmid vector. Protein was expressed as soluble protein with an N-terminal Histidine rich peptide tag suitable for immobilised metal affinity chromatography purification.

Cell stock was prepared in 50% glycerol and stored at −80° C. Glycerol stock strain was inoculated into LBA plates and subsequently incubated at 37° C. overnight. The content of each plate was washed with LB medium and diluted into 500 ml LB+AMP medium for expression. The cultures were incubated at 37° C. with shaking at 220 rpm until $OD_{600}$ 0.6 was reached. Succeeding induction was performed using 0.2 mM IPTG at 30° C. for 6 hours, giving a final $OD_{600}$ of 2.0. Cells were finally harvested by centrifugation.

Cells were subsequently suspended in 20 mM Tris-HCl, pH 8.5 and disrupted using a cell disrupter at 30 kPSI. The supernatant was collected by centrifugation and subsequently subjected to chromatographic purification.

The purification was performed using immobilised metal affinity chromatography as capturing step, followed by removal of the peptide tag using di-amino-peptidase from Unizyme. Final purification was achieved by ion-exchange chromatography. The purification could also be achieved by using but not limited to ion-exchange chromatography, hydrophobic interaction chromatography, affinity chromatography, size exclusion chromatography and membrane based separation techniques known to a person skilled in the art.

PEG groups were attached to the N-terminal by reacting the hGH compound with 2 equivalents of e.g. Peg-5000-aldehyde (RAPP Polymere, 12 5000-6). Reaction was initiated by addition of $NaCNBH_3$ in 0.5 ml MeCN in 10 steps. The reaction mixture was left for 20 h.

PEG groups were attached to Q40 by first reacting the hGH compound with 1,3-diamino-2-propanol (Fluka 33262) utilising microbial transglutaminase as catalyst.

Coupling of Transaminated and Oxidised hGH Compound (I) with a mPEG-Group.

The following solutions were prepared:
Buffer A: Triethanolamine (119 mg, 0.8 mmol) was dissolved in water (40 mL) and pH adjusted to 8.5.
Buffer B: 20 mM Triethanolamine; 0.2 M NaCl.
(A) Transamination of hGH (III) with 1,3-diamino-2-propanol
hGH (8.64 g) was dissolved in Buffer A (500 mL) with stirring. To this solution was added slowly a mixture of 1,3-diamino-2-propanol (DAP) (8.1 g, Fluka 33262) in Buffer A (50 mL). pH of the resulting mixture was adjusted to 8.5 by addition of aq. HCl. mTGase (2.8 mL, 1.3 mg/mL)) was added while mixing. The final mixture was stirred overnight at RT.
The reaction mixture was diluted with buffer A (1.2 L) and the product was purified by ion exchange chromatography. 100 mL/min-200 mL/frac.
Step Buffer B 40%-gradient 40-100% Buffer B over 15 CV=225 min.
(B) Oxidation of Transaminated hGH
Buffer A: Triethanolamine (119 mg, 0.8 mmol) was dissolved in water (40 mL) and pH adjusted to 8.5.
Buffer B: 3-methylthio-1-propanol (725 mg, 7.1 mmol) was dissolved in Buffer A (10 mL).
Buffer C: HEPES (5.96 g) was dissolved in water (1.0 L) and pH adjusted to 7.0
Periodate: $NaIO_4$ (48.1 mg, 0.225 mmol) was dissolved in water (1.0 mL).
To a solution of DAP reacted hGH (10 mg, 0.5 µmol) was added Buffer B (0.2 mL) followed by the periodate solution (0.03 mL). After 20 min's of cold incubation the mixture was dialyzed 4 times with buffer C. The residue was concentrated to 1 mL.
(C) Reductive Amination of Oxidised hGH with PEG-Reagent.
The final solution from (B) (1 mL, 0.45 µmol) was mixed with a PEG-amine solution (2 mL, 0.3 µmol) in 25 mM HEPES buffer pH 7.0 and the resulting mixture was slowly rotated at room temperature for 1 hr. After 1 hr $NaCNBH_3$ (100 µL of a solution of $NaCNBH_3$ (20 mg) in water (0.5 mL)) was added portion wise (10×). The mixture was kept at room temperature in the dark for 18-24 hours. The mixture was purified on a MonoQ, buffer changed and concentrated. mPEG-amine reagents are commercially available.

Example 2

Protein Chemical Characterization of Purified Growth Hormone Compounds

The intact purified protein was analysed using MALDI-MS. The observed mass corresponded to the theoretical mass deduced from the amino acid sequence.

The expected linkage of the three disulfide bonds in each compound was demonstrated by peptide mapping using trypsin and AspN digestion followed by MALDI-MS analysis of the digest before and after reduction of the disulfide bonds with DTT.

Example 3

Analysis of the Biological Activity of the Purified Growth Hormone Compounds

The biological activity of hGH compounds was measured in a cell based receptor potency proliferation assay, namely a BAF assay. The method is general for the hGH compounds.

The BAF-3 cells (a murine pro-B lymphoid cell line derived from the bone marrow) is IL-3 dependent for growth and survival. IL-3 activates JAK-2 and STAT which are the same mediators GH is activating upon stimulation.

The BAF-3 cells were transfected with a plasmid containing the hGH receptor. Clones able to proliferate upon stimulation with hGH were turned into hGH-dependent cell lines hereafter referred to as BAF3-GHR. The cell lines respond to GH with a dose-related growth pattern and can therefore be used to evaluate the effect of different hGH compounds in a proliferation assay.

The BAF-3 GHR cells are grown in starvation medium (culture medium without GH) for 24 hours at 37° C., 5% $CO_2$. The cells are centrifuged, the medium is removed and the cells are resuspended in starvation medium to $2.22 \times 10^5$ cells/ml. Portions of 90 µl of the cell supernatant are seeded into microtiter plates (96 well NUNC-clone). Different concentrations of growth hormone compound are added to the cells, and the plates are incubated for 72 hours at 37° C., 5% $CO_2$.

AlamarBlue is a redox indicator, AlamarBlue® (BioSource cat no Dal 1025) which is reduced by reactions innate to cellular metabolism and, therefore, provides an indirect measure of viable cell number. The AlamarBlue® is diluted 6 times (5 µl AlamarBlue®+25 µl stavation medium) and 30 µl of the diluted AlamarBlue® is added to each well. The cells are then incubated for another 4 hours. Finally the metabolic activity of the cells is measure in a fluorescence plate reader using an excitation filter of 544 nM and an emission filter of 590 nM.

The result for a given compound is expressed as the ratio between $EC_{50}$ of said compound and the $EC_{50}$ of wthGH run in parallel. Further results are given in table 6 below.

TABLE 2

EC50 values for hGH compounds relative to EC50 value for hGH

| Cys Compound | Average | Dev |
|---|---|---|
| A17C-E174C | 0.6 | 0.1 |
| H21C-M170C | 0.4 | 0.3 |
| R94C-D107C | 0.8 | 0.4 |
| Q84C-Y143C | 0.3 | 0.1 |
| S71C-S132C | 0.24 | 0.02 |

All hGH compounds tested were equipotent with or more potent than wthGH.

TABLE 2A

EC50 values for hGH compounds with a PEG group relative to EC50 value for hGH

| COMPOUND | EC50 BAF RATIO (hGH compound/hGH wt) |
|---|---|
| HGH | 1.0 |
| HGH (Q84C, Y143C) Q40-PEG5000 | 0.75 |
| HGH (Q84C, Y143C) N-TERM PEG750 | 0.475 |
| HGH (Q84C, Y143C) N-TERM PEG5000 | 1.1475 |

Example 3A

In Vivo Dose-Response Study in Hypophysectomised Sprague Dawley Rats (Assay 3A)

The in vivo dose-response relationship was studied in hypophysectomised male Sprague Dawley rats. The hypophysectomised rat is a well known and recognised animal model of growth hormone deficiency, where no production of growth hormone occurs after the surgical removal of the pituitary gland. This also leads to low circulating levels of insulin-like growth factor-1 (IGF-1) another important clinical feature of growth hormone deficiency in humans.

The hypophysectomy was performed on 4 week old male rats weighing 90-100 g. The animals entered the study 3-4 weeks after the surgery weighing 100-110 g. Animals with a body weight gain of more than 10% during the 3-4 weeks after surgery were not allowed to enter the study.

Seventy hypophysectomised Sprague Dawley rats were randomly allocated to seven dosing groups with ten animals in each group. One group received vehicle only and served as an untreated control group. Three groups received test compound (hGH Q84C, Y143C) 33, 3.3 and 0.33 nmol respectively and three groups received hGH as a comparator 50, 5.0 and 0.5 nmol respectively. Both compounds and vehicle were administered as a single subcutaneous dose in the neck. The body weight was measured daily between 8-10 am for one week.

Both hGH Q84C, Y143C and hGH induced a dose-dependent increase in body weight when body weight on Day 0 was compared to that of Day 7.

A sigmoidal dose-response equation was fitted to the experimental data (increase in body weight between Day 0-7) by non-linear regression analysis in order to calculate parameter estimates of $E_{max}$, $E_0$ and $ED_{50}$. The equation was a sigmoidal dose-response built-in equation in GraphPad Prism version 4.00 for Windows (GraphPad Software Inc., San Diego, USA). Data including parameter estimates and 95% confidence intervals are presented in Table 3.

No difference in parameter estimates of $E_0$ and $E_{max}$ was observed for hGH Q84C, Y143C and hGH. However $ED_{50}$ was significantly lower for hGH Q84C, Y143C compared to hGH indicating an increased in vivo potency of hGH Q84C, Y143C.

TABLE 3

The response as increase in body weight on Day 7 compared to Day 0 was fitted to a sigmoidal dose-response equation in order to estimate $E_{max}$, $E_0$ and $ED_{50}$.

| | hGH Q84C, Y143C | hGH wt |
|---|---|---|
| $E_0$ (g) | 0.0 | 0.2 |
| | (−1.9-1.8) | (−1.7-2.0) |
| $ED_{50}$ (nmol) | 0.29 | 0.70 |
| | (0.20-0.41) | (0.50-0.99) |
| $E_{max}$ (g) | 26.3 | 27.5 |
| | (24.8-27.9) | (25.9-29.1) |

Mean (95% confidence interval)

Example 4

Receptor Interaction Studies by Surface Plasmon Resonance Analysis

Receptor interaction of hGH compounds was analyzed using surface plasmon resonance analysis. The method is general for the hGH compounds and is exemplified by the Q84C/Y143C hGH compound.

The interaction of hGH and analogues with hGH binding protein (hGHBP) was studied by surface plasmon resonance using a Biacore T100 instrument (GE Healthcare, Sweden). Anti-hGH mAb (Fitzgerald Industries International, USA, #10G05B) was immobilized onto a CM-5 chip according to manufacturers instruction at a level of typically 5000 RU. wthGH or analogues were captured at 10-25 µg/ml in running buffer (10 mM HEPES, 0.15 M NaCl, 30 mM EDTA, 0.05% Surfactant P20, pH 7.4), which resulted in 250-400 RU captured ligand. hGHBP at a concentration of 0-800 nM was subsequently injected over the surface at 30 µl/min. A surface with immobilized anti-hGH mAb but without captured hGH was used as reference.

Kinetic data was analyzed with Biacore™ Evaluation Software 2.0 with the 1:1 Langmuir binding model.

Analysis showed (Table 4) that hGH Q84C, Y143C had similar or slightly higher affinity towards growth hormone binding protein than wthGH.

TABLE 4

| | ka (1/Ms) | kd (1/s) | KD (nM) |
|---|---|---|---|
| hGH wt | $1.9 \times 10^5$ | $6.1 \times 10^{-4}$ | 3.3 |
| hGH Q84C, Y143C | $2.0 \times 10^5$ | $4.8 \times 10^{-4}$ | 2.5 |

Analysis showed (Table 4A) that hGH Q84C, Y143C was equipotent with wild type hGH within the experimental error.

TABLE 4A

| | Ec50 ± std dev. (nM) |
|---|---|
| hGH wt | 0.7 ± 0.3 |
| hGH Q84C, Y143C | 0.3 ± 0.1 |

Example 5

Assay for Measuring Rate of Protease Degradation of Wild Type hGH and hGH Compounds The compound of interest is digested by a relevant protease (Trypsin, Chymotrypsin, Pepsin, Elastase, Factor VIIa, Factor Xa, Proteinase K, Carboxy peptidase, DPPIV, Neutral Endopeptidase, Granzyme B, Proline-endopeptidase, Staphylococcal peptidase I, Thermolysin, Thrombin, Arg-C proteinase, Asp-N endopeptidase, Caspase 1-10, Clostripain, Enterokinase, Glutamyl endopeptidase, Granzyme B, LysC, LysN, Proline-endopeptidase and Staphylococcal peptidase I or tissue extracts.) in an appropriate buffer (e.g. PBS or ammonium bicarbonate) at 37° C. for up till 24 hours. Proteolytic degradation is assessed by a HPLC assay.

General Method

Proteolytic Digestion:

100 μL of test compound solution at 1 mg/ml in ammonium bicarbonate buffer is degraded by enzyme for up till 24 hours at 37° C. Sub-samples are taken to various time points and the proteolytic reaction is stopped by acidifying the sample by 10 times dilution into 1 TFA. These diluted samples are analysed by reversed phase HPLC to estimate the degree of proteolytic digestion.

HPLC Method:

10 μL of the above solution is injected on a reversed phase Vydac C4 2×150 mm column eluted with a linear gradient from 0.1% TFA in water to 100% acetonitrile containing 0.1% TFA over a period of 30 min at a flow rate of 0.2 ml/min. Detection of peaks is performed at 214 nm UV absorption. % intact compound at time point t=T is calculated from the peak area at time point t=T ($A_T$) and the peak area at t=0 ($A_0$) as ($A_T/A_0$)×100%. The results provided in table 6 here below were obtained after 4 hours (T=4 in above equation).

% intact compound is plotted against time using GraphPad Prims software ver. 5.01. T½ is calculated as one phase decay also by GraphPad Prism software.

Enzymes used in the example are elastase (Sigma from porcine pancrease) and chymotrypsin (Roche sequencing grade). Buffer is 50 mM ammonium bicarbonate pH 8.5.

Example 5.1

100 μg of wthGH was incubated in 100 μL buffer with 13 ng of chymotrypsin. T½=3.6 hours.

Example 5.2

100 μg of wthGH was incubated in 100 μL buffer with 135 ng of elastase. T½=1.6 hours.

Example 5.3

100 μg of hGH Q84C, Y143C was incubated in 100 μL buffer with 135 ng of elastase. T½=6.2 hours.

Example 5.4

100 μg of hGH A17C, E174C was incubated in 100 μL buffer with 13 ng of chymotrypsin. T½=7.5 hours.

Example 5.5

100 μg of hGH H21C, M170C was incubated in 100 μL buffer with 13 ng of chymotrypsin. T½=22 hours

Example 5.6

100 μg of hGH R94C, D107C was incubated in 100 μL buffer with 13 ng of chymotrypsin. T½=2.5 hours.

Example 5.7

100 μg of hGH Q84C, Y143C was incubated in 100 μL 50 mM ammonium bicarbonate buffer pH 8.5 with 13 ng of chymotrypsin. T½ can not be calculated as no degradation is observed.

TABLE 4

| T½ (hours) for degradation of wild type hGH and compounds by chymotrypsin | |
|---|---|
| Compound | T½ |
| hGH wt | 3.6 |
| hGH A17C, E174C | 7.5 |
| hGH H21C, M170C | 22 |
| hGH R94C, D107C | 2.5 |
| hGH Q84, Y143C | N/A |

TABLE 5

| T½ (hours) for degradation of wild type hGH and the hGH Q84C, Y143C compound by elastase. | |
|---|---|
| Compound | T½ |
| hGH wt | 1.6 |
| hGH Q84C, Y143C | 6.2 |

Example 6

Analysis of Selected Compounds by BAF Assay and Proteolytic Digestion as Described in Example 3 and Example 5

TABLE 6

Analysis of growth hormone compounds comprising additional disulfide bonds.

| Compound | EC50 BAF Ratio (hGH compound/hGH) | Chymotrypsin stability Intact compound (%) | Elastase stability Intact compound (%) | Domains linked by additional disulfide bond |
|---|---|---|---|---|
| HGH | 1.0 | 42 | 25 | |
| HGH (A17C E174C) | 0.6 | 45 | 10 | H1-H4 |
| HGH (H21C M170C) | 0.5 | 72 | 10 | H1-H4 |
| HGH (D26C, V102C) | 0.5 | 55 | 65 | H1-L2 |
| HGH (D26C, Y103C) | 0.5 | 55 | 45 | H1-L2 |
| HGH (F54C, Y143C) | 0.6 | 55 | 20 | L1-L3 |
| HGH (F54C, S144C) | 0.5 | 60 | 20 | L1-L3 |

TABLE 6-continued

Analysis of growth hormone compounds comprising additional disulfide bonds.

| Compound | EC50 BAF Ratio (hGH compound/hGH) | Chymotrypsin stability Intact compound (%) | Elastase stability Intact compound (%) | Domains linked by additional disulfide bond |
|---|---|---|---|---|
| HGH (F54C, F146C) | 0.6 | 40 | 25 | L1-L3 |
| HGH (S55C, Y143C) | 0.5 | 90 | 25 | L1-L3 |
| HGH (S57C, Y143C) | 0.3 | 75 | 50 | L1-L3 |
| HGH (I58C Q141C) | 0.7 | 70 | 25 | L1-L3 |
| HGH (I58C, Y143C) | 0.6 | 55 | 20 | L1-L3 |
| HGH (I58C, S144C) | 1.2 | 65 | 30 | L1-L3 |
| HGH (P59C Q137C) | 0.7 | 72 | 35 | L1-L3 |
| HGH (S71C S132C) | 0.2 | 90 | 45 | L1-L3 |
| HGH (L81C, Y143C) | 0.7 | 85 | 15 | H2-L3 |
| HGH (Q84C Y143C) | 0.5 | 100 | 80 | H2-L3 |
| HGH (S85C Y143C) | 0.5 | 80 | 70 | H2-L3 |
| HGH (S85C, S144C) | 0.7 | 81 | 60 | H2-L3 |
| HGH (F92C, T148C) | 0.6 | 40 | 55 | H2-L3 |
| HGH (R94C D107C) | 0.8 | 38 | 70 | H2-H3 |

The invention claimed is:

1. A growth hormone compound comprising a polypeptide having an amino acid sequence that is at least 95% identical to SEQ ID NO: 1, wherein the polypeptide comprises an additional disulfide bond between a loop segment and a helical segment, or within a loop segment, or between loop segments, or between helical segments of the polypeptide.

2. A growth hormone compound according to claim 1, wherein the amino acid sequence of the polypeptide is at least 96%, at least 97%, or at least 98% identical to SEQ ID NO: 1.

3. The growth hormone compound of claim 1, wherein the polypeptide comprises at least one pair of mutations selected from the group consisting of R16C/L117C, A17C/E174C, H21C/M 170C, D26/V 102C, D26/Y 103C, N47C/T50C, Q49C/G 161 C, F54C/Y 143C, F54C/S 144C, F54C/F146C, S55C/Y143C, S57C/Y143C, I58C/Q141C, I58C/Y143C, I58C/S144C, P59C/Q137C, P61C/E66C, P61C/T67C, S71C/S132C, L73C/S132C, L73C/F139C, R77C/I138C, R77C/F139C, L81C/Q141C, L81C/Y143C, Q84C/Y143C, Q84C/S 144C, S85C/Y143C, S85C/S144C, P89C/F 146C, F92C/F 146C, F92C/T 148C, R94C/D 107C, V 102C/A 105C, L156C/F 146C, L156C/T148C and V185C/S188C in SEQ ID NO: 1.

4. The growth hormone compound of claim 3, wherein the polypeptide comprises at least one pair of mutations selected from the group consisting of A17C/E174C, H21C/M 170C, D26/V 102C, D26/Y 103C, F54C/Y 143C, F54C/S 144C, F54C/F 146C, S55C/Y 143C, S57C/Y143C, I58C/Q141C, I58C/Y143C, I58C/S144C, P59C/Q137C, S71C/S132C, L81C/Y143C, Q84C/Y143C, S85C/Y143C, S85C/S144C, F92C/T148C and R94C/D107C in SEQ ID NO: 1.

5. The growth hormone compound of claim 1, wherein the polypeptide comprises an additional disulfide bond wherein at least one of the cysteines is present in loop 3 (L3) corresponding to amino acids 128-154 of SEQ ID NO: 1.

6. The growth hormone compound of claim 5, wherein the polypeptide comprises at least one pair of mutations selected from the group consisting of F54C/Y143C, F54C/S144C, F54C/F146C, S55C/Y143C, S57C/Y143C, I58C/Q141C, I58C/Y143C, I58C/S144C, P59C/Q137C, S71C/S132C, L73C/S132C, L73C/F139C, R77C/I138C, R77C/F139C, L81C/Q141C, L81C/Y143C, Q84C/Y143C, Q84C/S 144C, S85C/Y143C, S85C/S 144C, P89C/F146C, F92C/F146C and F92C/T148C in SEQ ID NO: 1.

7. The growth hormone compound of claim 5, wherein the polypeptide comprises an additional disulfide bond connecting L3 with helix 2 (H2) or loop 1 (L1).

8. The growth hormone of claim 1, wherein the polypeptide comprises an additional disulfide bond wherein at least one of the cysteines is present in a region corresponding to amino acids 135-148 of SEQ ID NO: 1.

9. The growth hormone compound of claim 1, wherein the growth hormone compound is stabilized towards degradation by a protease.

10. The growth hormone compound of claim 1, wherein the polypeptide comprises at least one pair of mutations selected from the group consisting of H21C/M170C, D26C/V102C, D26C/Y103C, F54C/Y143C, F54C/S 144C, S55C/Y143C, S57C/Y143C, I58C/Q141C, I58C/Y143C, I58C/S 144C, P59C/Q137C, S71C/S 132C, L81C/Y143C, Q84C/Y143C, S85C/Y143C, S85C/S144C, F92C/T148C and R94C/D107C in SEQ ID NO:1.

11. The growth hormone compound of claim 1, wherein the polypeptide comprises exactly two additional cysteines compared to SEQ ID NO: 1 (human growth hormone).

12. A method for preparing the growth hormone compound of claim 1, wherein the polypeptide has increased stability towards proteolytic degradation, comprising the step of introducing an additional disulfide bond into human growth hormone (hGH) as defined in SEQ ID NO: 1.

13. A pharmaceutical composition comprising the growth hormone compound of claim 1 and a pharmaceutically acceptable carrier/s.

14. A method of treating a disease wherein a patient will benefit from an increase in the amount of circulating growth hormone, said method comprising administering to patient an effective amount of the composition of claim 13.

* * * * *

UNITED STATES PATENT AND TRADEMARK OFFICE
CERTIFICATE OF CORRECTION

PATENT NO. : 8,513,192 B2  Page 1 of 1
APPLICATION NO. : 13/144757
DATED : August 20, 2013
INVENTOR(S) : Ole H. Olsen et al.

It is certified that error appears in the above-identified patent and that said Letters Patent is hereby corrected as shown below:

In the Claims

Column 40, claim 13, line number 54, delete "…and pharmaceutically acceptable carrier/s" and insert --…and one or more pharmaceutically acceptable carriers--.

Signed and Sealed this
Third Day of June, 2014

Michelle K. Lee
*Deputy Director of the United States Patent and Trademark Office*

SEQUENCE LISTING

<160> NUMBER OF SEQ ID NOS: 1

<210> SEQ ID NO 1
<211> LENGTH: 191
<212> TYPE: PRT
<213> ORGANISM: Homo sapiens
<220> FEATURE:
<221> NAME/KEY: MISC_FEATURE
<222> LOCATION: (6)..(35)
<223> OTHER INFORMATION: Helix 1
<220> FEATURE:
<221> NAME/KEY: MISC_FEATURE
<222> LOCATION: (36)..(71)
<223> OTHER INFORMATION: Loop 1
<220> FEATURE:
<221> NAME/KEY: MISC_FEATURE
<222> LOCATION: (72)..(98)
<223> OTHER INFORMATION: Helix 2
<220> FEATURE:
<221> NAME/KEY: MISC_FEATURE
<222> LOCATION: (99)..(106)
<223> OTHER INFORMATION: Loop 2
<220> FEATURE:
<221> NAME/KEY: MISC_FEATURE
<222> LOCATION: (107)..(127)
<223> OTHER INFORMATION: Helix 3
<220> FEATURE:
<221> NAME/KEY: MISC_FEATURE
<222> LOCATION: (128)..(154)
<223> OTHER INFORMATION: Loop 3
<220> FEATURE:
<221> NAME/KEY: MISC_FEATURE
<222> LOCATION: (155)..(184)
<223> OTHER INFORMATION: Helix 4

<400> SEQUENCE: 1

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
                20                  25                  30

Glu Ala Tyr Ile Pro Lys Glu Gln Lys Tyr Ser Phe Leu Gln Asn Pro
            35                  40                  45

Gln Thr Ser Leu Cys Phe Ser Glu Ser Ile Pro Thr Pro Ser Asn Arg
        50                  55                  60

Glu Glu Thr Gln Gln Lys Ser Asn Leu Glu Leu Leu Arg Ile Ser Leu
65                  70                  75                  80

-continued

```
Leu Leu Ile Gln Ser Trp Leu Glu Pro Val Gln Phe Leu Arg Ser Val
            85                  90                  95

Phe Ala Asn Ser Leu Val Tyr Gly Ala Ser Asp Ser Asn Val Tyr Asp
           100                 105                 110

Leu Leu Lys Asp Leu Glu Gly Ile Gln Thr Leu Met Gly Arg Leu
           115             120             125

Glu Asp Gly Ser Pro Arg Thr Gly Gln Ile Phe Lys Gln Thr Tyr Ser
        130             135             140

Lys Phe Asp Thr Asn Ser His Asn Asp Asp Ala Leu Leu Lys Asn Tyr
145                 150             155                 160

Gly Leu Leu Tyr Cys Phe Arg Lys Asp Met Asp Lys Val Glu Thr Phe
                165             170             175

Leu Arg Ile Val Gln Cys Arg Ser Val Glu Gly Ser Cys Gly Phe
             180             185             190
```